United States Patent
Chang et al.

(10) Patent No.: US 9,745,329 B1
(45) Date of Patent: Aug. 29, 2017

(54) METHOD OF PREPARING SILYLATIVE-REDUCED N-HETEROCYCLIC COMPOUND USING ORGANOBORON CATALYST

(71) Applicants: INSTITUTE FOR BASIC SCIENCE, Daejeon (KR); KOREA ADVANCED INSTITUTE OF SCIENCE AND TECHNOLOGY, Daejeon (KR)

(72) Inventors: Sukbok Chang, Daejeon (KR); Sehoon Park, Daejeon (KR); Narasimhulu Gandhamsetty, Andhra Pradhesh (IN); Seewon Joung, Daejeon (KR); Sung-Woo Park, Daejeon (KR)

(73) Assignees: Institute for Basic Science, Daejeon (KR); Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 14/891,096

(22) PCT Filed: Jan. 29, 2015

(86) PCT No.: PCT/KR2015/000994
§ 371 (c)(1),
(2) Date: Nov. 13, 2015

(87) PCT Pub. No.: WO2016/076479
PCT Pub. Date: May 19, 2016

(30) Foreign Application Priority Data

Nov. 11, 2014 (KR) .................. 10-2014-0156194

(51) Int. Cl.
C07F 7/08 (2006.01)
(52) U.S. Cl.
CPC .......... C07F 7/0896 (2013.01); C07F 7/0836 (2013.01); C07F 7/0874 (2013.01)
(58) Field of Classification Search
CPC ..... C07F 7/0896; C07F 7/0836; C07F 7/0874
See application file for complete search history.

(56) References Cited

PUBLICATIONS

Chernyak, J Am Chem SOc, 2010, vol. 132, 8270-8272.*
Ikzuka, Eru J Org Chem, 2008, 1161-1163.*
Baliah, V. et al., "Synthesis of 2,6-Distributed Piperidines, Oxanes, and Thianes," Chemical Reviews, vol. 83, No. 4, Aug. 1983, 45 pages.
Katritzky, A. et al., "Recent Progress in the Synthesis of 1,2,3,4-Tetrahydroquinolines," Tetrahedron, vol. 52, No. 48, Report No. 410, Nov. 25, 1996, 40 pages.
Gribble, G., "Sodium Borohydride in Carboxylic Acid Media: A Phenomenal Reduction System," Chemical Society Reviews, vol. 26, No. 6, Jan. 1, 1998, 10 pages.
Bianchini, C. et al., "Hydrogenation of Quinoline by Rhodium Catalysts Modified with the Tripodal Polyphosphine Ligand MeC(CH2PPh2)3," Helvetica Chimica Acta, vol. 84, No. 10, Oct. 27, 2001, 29 pages.
Rubin, M. et al., "Highly Efficient B(C6F5)3-Catalyzed Hydrosilylation of Olefins," Journal of Organic Chemistry, vol. 67, No. 6, Mar. 22, 2002, Published Online Feb. 26, 2002, 5 pages.
Kallstrom, S. et al., "Synthesis of Pharmaceutically Active Compounds Containing a Distributed Piperidine Framework," Bioorganic & Medicinal Chemistry, vol. 16, No. 2, Jan. 15, 2008, Published Online Oct. 12, 2007, 35 pages.
Geier, S. et al., "Metal-free Reductions of N-Heterocycles via Lewis Acid Catalyzed Hydrogenation," The Royal Society of Chemistry (Supplementary Material (ESI) for Chemical Communications), 2010, 3 pages.
Gutsalyak, D. et al., "Facile Catalytic Hydrosilylation of Pyridines," Angewandte Chemie (International ed. in English), vol. 50, No. 6, Feb. 7, 2011, Published Online Jan. 5, 2011, 4 pages.
Simonneau, A. et al., "3-Silylated Cyclohexa-1,4-dienes as Precursors for Gaseous Hydrosilanes: The B(C6F5)3-Catalyzed Transfer Hydrosilylation of Alkenes," Angewandte Chemie (International ed. in English), vol. 52, No. 45, Nov. 4, 2013, Published Online Sep. 17, 2013, 3 pages.
Sakata, K. et al., "Quantum Chemical Study of B(C6F5)3-Catalyzed Hydrosilylation of Carbonyl Group," Journal of Organic Chemistry, vol. 78, No. 24, Dec. 20, 2013, Published Online Nov. 13, 2013, 8 pages.
ISA Korean Intellectual Property Office, International Search Report Issued in Application No. PCT/KR2015/000994, Jul. 1, 2015, WIPO, 3 pages.
ISA Korean Intellectual Property Office, Written Opinion Issued in Application No. PCT/KR2015/000994, Jul. 1, 2015, WIPO, 3 pages.

* cited by examiner

Primary Examiner — D M Seaman
(74) Attorney, Agent, or Firm — McCoy Russell LLP

(57) ABSTRACT

Provided is a method of preparing a silylative-reduced N-heterocyclic compound by reducing an N-heteroaromatic compound including a $sp^2$ hybridized nitrogen atom while simultaneously introducing a silyl group into a beta-position with respect to a nitrogen atom of the N-heteroaromatic compound, using a silane compound, in the presence of an organoboron catalyst.

10 Claims, No Drawings

METHOD OF PREPARING SILYLATIVE-REDUCED N-HETEROCYCLIC COMPOUND USING ORGANOBORON CATALYST

CROSS REFERENCE TO RELATED APPLICATIONS

The present application is a U.S. National Phase of International Patent Application Serial No. PCT/KR2015/000994, entitled "METHOD OF PREPARING SILYLATIVE-REDUCED N-HETEROCYCLIC COMPOUND USING ORGANOBORON CATALYST," filed on Jan. 29, 2015, which claims priority to Korean Patent Application No. 10-2014-0156194, entitled "METHOD OF PREPARING SILYLATIVE-REDUCED N-HETEROCYCLIC COMPOUND USING ORGANOBORON CATALYST," filed on Nov. 11, 2014, the entire contents of each of which are hereby incorporated by reference for all purposes.

TECHNICAL FIELD

The present invention relates to a method of preparing a silylative-reduced N-heterocyclic compound by reducing an N-heteroaromatic compound including a $sp^2$ hybridized nitrogen atom while simultaneously introducing a silyl group into a beta-position with respect to a nitrogen atom of the N-heteroaromatic compound, using a silane compound, in the presence of an organoboron catalyst.

BACKGROUND ART

A heterocyclic compound has a basic framework of a natural product, and in particular, a piperidine-based derivative and a tetrahydroquinoline-based derivative, having a substituent, are widely used as an important intermediate and an important synthetic unit in pharmaceutical industries such as alkaloids, pharmaceutical products and agrichemical products, and material industries, such that methods of preparing these derivatives have been variously researched.

As a method of synthesizing the piperidine-based derivative and the tetrahydroquinoline-based derivative, having the substituent, a reduction method of N-heteroaromatic cyclic compounds such as a pyridine-based derivative and a quinoline-based derivative has been known.

In the reduction of the N-heteroaromatic cyclic compound has a significantly high reaction barrier, unlike a reduction of a hydrocarbon-aromatic cyclic compound, there is deactivation or poisoning pathway with respect to a reducing agent or a catalyst due to high basicity of a $sp^3$-nitrogen atom newly produced from a reaction product, and there are no chemical- and regio-selectivity, which is partially reduced.

One of the known reduction methods of the N-heteroaromatic cyclic compound is to use a stoichiometric metal hydride including $NaBH_4$, $LiAlH_4$ or reactive metals (for example: Na), which may have problems such as limited ranges of starting materials, a large amount of waste, and the like, in addition to the above-described problems.

In addition, a reduction reaction of the N-heteroaromatic cyclic compound using hydrogen gas ($H_2$) under a metal-mediated condition or a metal-free condition is also performed under high pressure ($H_2$) and increased temperature, which causes formation of excessively reduced products, such that there is a limitation in introducing functional groups.

Further, in the case of a reduction method of the N-heteroaromatic cyclic compound using hydrosilane under a metal-mediated condition, partially reduced products may be formed, which do not have regioselectivity.

That is, as described above, the existing reduction of the N-heteroaromatic cyclic compound requires severe reaction conditions or shows low regioselectivity through multi-steps, and sometimes requires the use of high-priced metal catalyst.

Therefore, there is a need for a simpler and economical process under a mild condition, completely excluding the severe reaction conditions, the multi-step synthesis, and the use of high-priced metal catalyst required in the existing known methods.

RELATED ART DOCUMENT

Non-Patent Document (Non-Patent Document 1) *Chem. Rev.* 83, 379-423 (1983).
(Non-Patent Document 2) *Bioorganic & Medicinal Chemistry.* 16, 601-635 (2008).
(Non-Patent Document 3) *Tetrahedron.* 52, 15031-15070 (1996).
(Non-Patent Document 4) *Chem. Soc. Rev.* 27, 395-404 (1998).
(Non-Patent Document 5) *Helvetica Chimica Acta.* 84, 2895-2923 (2001).
(Non-Patent Document 6) *Angew. Chem., Int. Ed.* 50, 1384-1387 (2011).

DISCLOSURE

Technical Problem

The present inventors studied an introduction of a substituent having excellent selectivity and a reduction reaction, using a simple and low-priced organic catalyst without including a metal under a mild condition, as a result, found that an N-heterocyclic compound into which an organic silyl group is introduced at a specific position is capable of being prepared by performing regioselective silylation of an N-heteroaromatic compound including a $sp^2$ hybridized nitrogen atom while simultaneously reducing an N-resonance structure, using a simple secondary to tertiary organic silane compound on the market as a reducing agent, in the presence of an organoboron catalyst, and completed the present invention.

An object of the present invention is to provide a method of preparing a silylative-reduced N-heterocyclic compound by reducing an N-heteroaromatic compound including a $sp^2$ hybridized nitrogen atom while simultaneously introducing a silyl group into a beta-position with respect to a nitrogen atom of the N-heteroaromatic compound, using a silane compound, in the presence of an organoboron catalyst.

Technical Solution

In one general aspect, there is provided a method of preparing an N-heterocyclic compound into which an organic silyl group is introduced at a specific position, usable as an intermediate and a synthetic unit which are important for synthesis of various pharmaceutical products and agrichemical products, more specifically, a method of preparing a silylative-reduced N-heterocyclic compound by reducing an N-heteraromatic compound including a central ring having 5 to 20 carbon atoms and a $sp^2$ hybridized nitrogen atom while simultaneously introducing a silyl group into a beta-position with respect to a nitrogen atom of the N-heteroaromatic compound, using a silane compound, in the presence of an organoboron catalyst.

In an exemplary embodiment of the present invention, the N-heteroaromatic compound including a central ring having 5 to 20 carbon atoms and a sp² hybridized nitrogen atom may be of a single ring type or a fused ring type, and may be represented by the following Chemical Formulas 2-1 to 2-5. However, the present invention is not limited thereto:

[Chemical Formula 2-1]

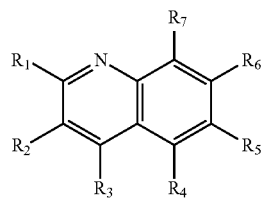

[Chemical Formula 2-2]

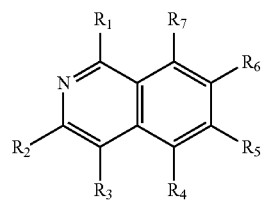

[Chemical Formula 2-3]

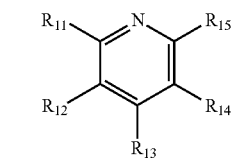

[Chemical Formula 2-4]

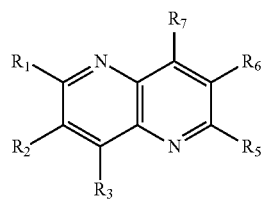

[Chemical Formula 2-5]

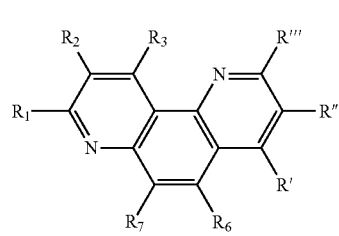

in Chemical Formulas 2-1 to 2-5, $R_1$ to $R_7$, R', R" and R'" are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12)alkenylene with or without a fused ring to form a monocyclic or polycyclic aromatic ring;

$R_{11}$ to $R_{15}$ are each independently hydrogen, (C1-C10)alkyl, (C1-C10)alkoxy, (C6-C12)aryl, halogen or (C6-C12)aryloxy; and the alkyl, aryl and aryloxy of $R_1$ to $R_7$ and $R_{11}$ to $R_{15}$ may be further substituted with (C1-C10)alkyl.

In an exemplary embodiment of the present invention, the silane compound may be represented by the following Chemical Formulas 3-1 to 3-3:

[Chemical Formula 3-1]

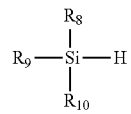

[Chemical Formula 3-2]

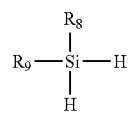

[Chemical Formula 3-3]

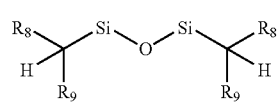

in Chemical Formulas 3-1 to 3-3, $R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

In an exemplary embodiment of the present invention, the silylative-reduced N-heterocyclic compound may be represented by the following Chemical Formulas 1-1 to 1-7, and 5-1 to 5-5:

[Chemical Formula 1-1]

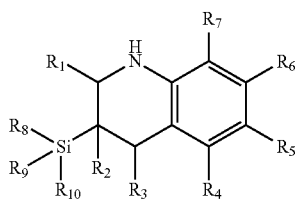

[Chemical Formula 1-2]

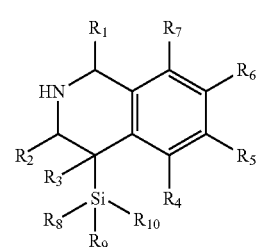

[Chemical Formula 1-3]

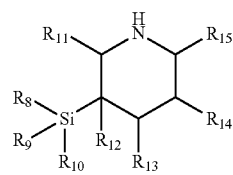

[Chemical Formula 1-4]

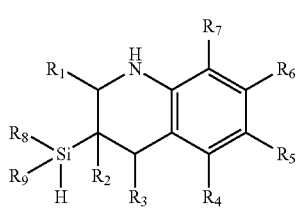

[Chemical Formula 1-5]

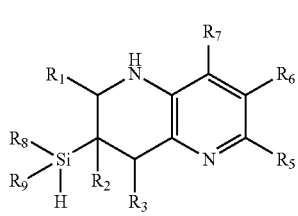

[Chemical Formula 1-6]

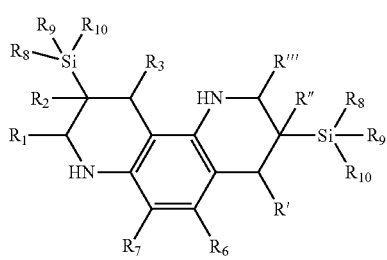

[Chemical Formula 1-7]

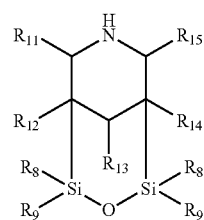

[Chemical Formula 5-1]

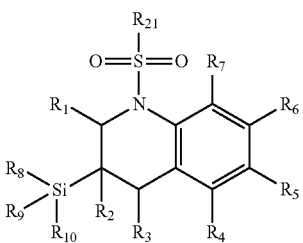

[Chemical Formula 5-2]

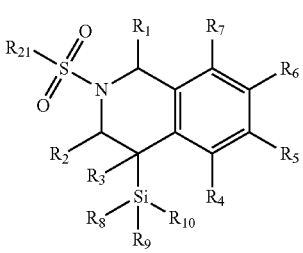

[Chemical Formula 5-3]

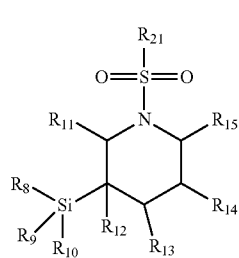

[Chemical Formula 5-4]

[Chemical Formula 5-5]

In Chemical Formulas 1-1 to 1-7, and 5-1 to 5-5, $R_1$ to $R_7$, R', R" and R''' are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12)alkenylene with or without a fused ring to form a monocyclic or polycyclic aromatic ring;

$R_{11}$ to $R_{15}$ are each independently hydrogen, (C1-C10)alkyl, (C1-C10)alkoxy, (C6-C12)aryl, halogen or (C6-C12)aryloxy;

$R_8$ and $R_9$ are each independently (C1-C10)alkyl or (C6-C12)aryl;

$R_{10}$ is hydrogen or (C6-C12)aryl;

$R_{21}$ is (C3-C10)heteroaryl or (C6-C12)aryl, and the heteroaryl and aryl independently may be further substituted with at least one selected from (C1-C10)alkyl, halo(C1-C10)alkyl, (C6-C12)aryl, (C3-C10)cycloalkyl, cyano, halogen, and nitro; and the alkyl, aryl and aryloxy of $R_1$ to $R_7$ and $R_{11}$ to $R_{15}$ may be further substituted with (C1-C10)alkyl;

provided that $R_8$, $R_9$ and $R_{10}$ are not (C6-C12)aryl at the same time.

In the method of preparing the silylative-reduced N-heterocyclic compound according to an exemplary embodiment of the present invention, an N-heterocyclic compound represented by the following Chemical Formula 1-1 may be prepared by reacting a quinoline compound represented by the following Chemical Formula 2-1 with a silane compound represented by the following Chemical Formula 3-1, in the presence of the organoboron catalyst:

[Chemical Formula 1-1]

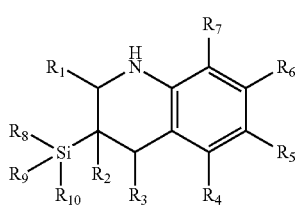

[Chemical Formula 2-1]

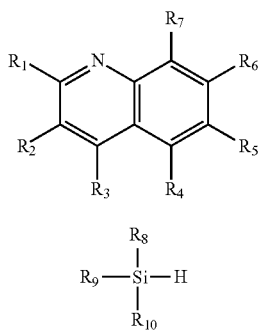

[Chemical Formula 3-1]

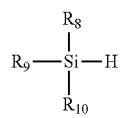

in Chemical Formulas 1-1, 2-1, and 3-1, $R_1$ to $R_7$ are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12)alkenylene with or without a fused ring to form a monocyclic or polycyclic aromatic ring, and the alkyl, aryl and aryloxy of $R_1$ to $R_7$ may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

The method of preparing the silylative-reduced N-heterocyclic compound according to an exemplary embodiment of the present invention may include: 1) preparing an N-heterocyclic compound represented by the following Chemical Formula 1-1 by reacting a quinoline compound represented by the following Chemical Formula 2-1 with a silane compound represented by the following Chemical Formula 3-1, in the presence of the organoboron catalyst; and 2) preparing an N-heterocyclic compound represented by the following Chemical Formula 5-1 by reacting the N-heterocyclic compound represented by Chemical Formula 1-1 prepared from step 1) above with a sulfonyl halide compound represented by the following Chemical Formula 4:

[Chemical Formula 5-1]

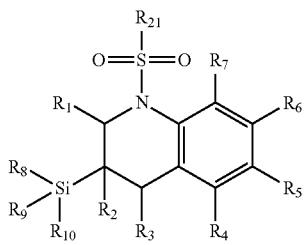

[Chemical Formula 2-1]

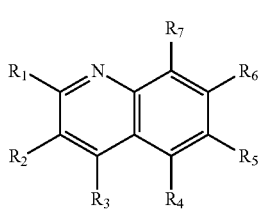

[Chemical Formula 3-1]

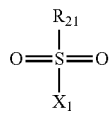

[Chemical Formula 1-1]

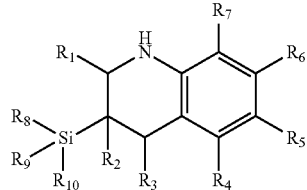

[Chemical Formula 4]

$$O=\underset{X_1}{\overset{R_{21}}{\underset{\|}{S}}}=O$$

in Chemical Formulas 1-1, 2-1, 3-1, 4 and 5-1, $R_1$ to $R_7$ are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12)alkenylene with or without a fused ring to form a monocyclic or polycyclic aromatic ring, and the alkyl, aryl and aryloxy of $R_1$ to $R_7$ may be further substituted with (C1-C10)alkyl;

$R_8$ and $R_9$ are each independently (C1-C10)alkyl or (C6-C12)aryl;

$R_{10}$ is hydrogen or (C6-C12)aryl;

$R_{21}$ is (C3-C10)heteroaryl or (C6-C12)aryl, and the heteroaryl and aryl may be independently further substituted with at least one selected from (C1-C10)alkyl, halo(C1-C10)alkyl, (C6-C12)aryl, (C3-C10)cycloalkyl, cyano, halogen, and nitro; and $X_1$ is halogen;

provided that $R_8$, $R_9$ and $R_{10}$ are not (C6-C12)aryl at the same time.

In the method of preparing the silylative-reduced N-heterocyclic compound according to an exemplary embodiment of the present invention, an N-heterocyclic compound represented by the following Chemical Formula 1-2 may be prepared by reacting an isoquinoline compound represented by the following Chemical Formula 2-2 with a silane compound represented by the following Chemical Formula 3-1, in the presence of the organoboron catalyst:

[Chemical Formula 1-2]

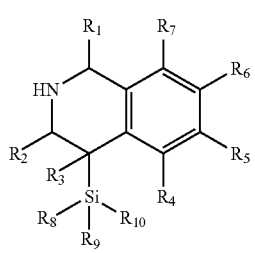

-continued

[Chemical Formula 2-2]

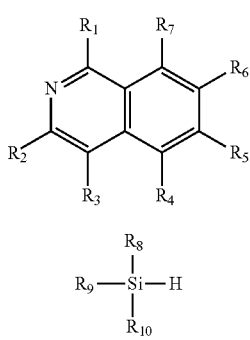

[Chemical Formula 3-1]

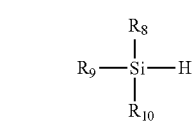

in Chemical Formulas 1-2, 2-2, and 3-1, $R_1$ to $R_7$ are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12)alkenylene with or without a fused ring to form a monocyclic or polycyclic aromatic ring, and the alkyl, aryl and aryloxy of $R_1$ to $R_7$ may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

The method of preparing the silylative-reduced N-heterocyclic compound according to an exemplary embodiment of the present invention may include: 1) preparing an N-heterocyclic compound represented by the following Chemical Formula 1-2 by reacting an isoquinoline compound represented by the following Chemical Formula 2-2 with a silane compound represented by the following Chemical Formula 3-1, in the presence of the organoboron catalyst; and 2) preparing an N-heterocyclic compound represented by the following Chemical Formula 5-2 by reacting the N-heterocyclic compound represented by the Chemical Formula 1-2 prepared from step 1) above with a sulfonyl halide compound represented by the following Chemical Formula 4:

[Chemical Formula 5-2]

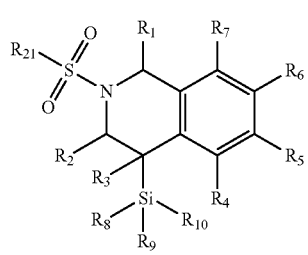

[Chemical Formula 2-2]

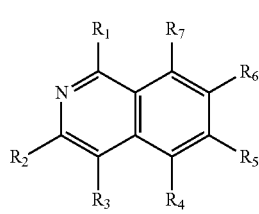

[Chemical Formula 3-1]

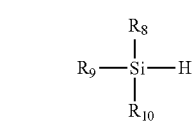

-continued

[Chemical Formula 1-2]

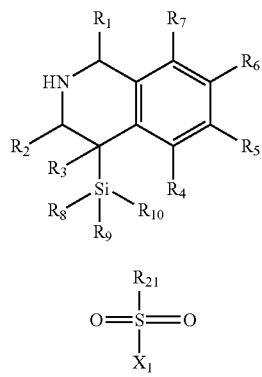

[Chemical Formula 4]

$$O=\underset{X_1}{\overset{R_{21}}{\underset{\|}{S}}}=O$$

in Chemical Formulas 1-2, 2-2, 3-1, 4 and 5-2, $R_1$ to $R_7$ are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12)alkenylene with or without a fused ring to form a monocyclic or polycyclic aromatic ring, and the alkyl, aryl and aryloxy of $R_1$ to $R_7$ may be further substituted with (C1-C10)alkyl;

$R_8$ and $R_9$ are each independently (C1-C10)alkyl or (C6-C12)aryl;

$R_{10}$ is hydrogen or (C6-C12)aryl;

$R_{21}$ is (C3-C10)heteroaryl or (C6-C12)aryl, and the heteroaryl and aryl may be independently further substituted with at least one selected from (C1-C10)alkyl, halo(C1-C10)alkyl, (C6-C12)aryl, (C3-C10)cycloalkyl, cyano, halogen, and nitro; and $X_1$ is halogen;

provided that $R_8$, $R_9$ and $R_{10}$ are not (C6-C12)aryl at the same time.

In the method of preparing the silylative-reduced N-heterocyclic compound according to an exemplary embodiment of the present invention, an N-heterocyclic compound represented by the following Chemical Formula 1-3 may be prepared by reacting a pyridine compound represented by the following Chemical Formula 2-3 with a silane compound represented by the following Chemical Formula 3-1, in the presence of the organoboron catalyst:

[Chemical Formula 1-3]

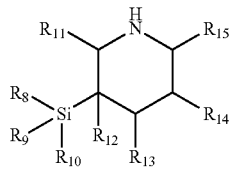

[Chemical Formula 2-3]

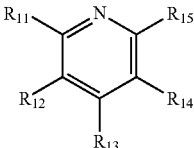

[Chemical Formula 3-1]

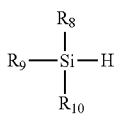

in Chemical Formulas 1-3, 2-3, and 3-1, $R_{11}$ to $R_{15}$ are each independently hydrogen, (C1-C10)alkyl, (C1-C10)alkoxy, (C6-C12)aryl, halogen or (C6-C12)aryloxy, and the alkyl, aryl and aryloxy of $R_{11}$ to $R_{15}$ may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

The method of preparing the silylative-reduced N-heterocyclic compound according to an exemplary embodiment of the present invention may include: 1) preparing an N-heterocyclic compound represented by the following Chemical Formula 1-3 by reacting a pyridine compound represented by the following Chemical Formula 2-3 with a silane compound represented by the following Chemical Formula 3-1, in the presence of the organoboron catalyst; and 2) preparing an N-heterocyclic compound represented by the following Chemical Formula 5-3 by reacting the N-heterocyclic compound represented by Chemical Formula 1-3 prepared from step 1) above with a sulfonyl halide compound represented by the following Chemical Formula 4:

$R_{10}$ is hydrogen or (C6-C12)aryl;

$R_{21}$ is (C3-C10)heteroaryl or (C6-C12)aryl, and the heteroaryl and aryl may be independently further substituted with at least one selected from (C1-C10)alkyl, halo(C1-C10)alkyl, (C6-C12)aryl, (C3-C10)cycloalkyl, cyano, halogen, and nitro; and $X_1$ is halogen;

provided that $R_8$, $R_9$ and $R_{10}$ are not (C6-C12)aryl at the same time.

The method of preparing the silylative-reduced N-heterocyclic compound according to an exemplary embodiment of the present invention may include: 1) preparing an N-heterocyclic compound represented by the following Chemical Formula 1-4 by reacting a quinoline compound represented by the following Chemical Formula 2-1 with a silane compound represented by the following Chemical Formula 3-2, in the presence of the organoboron catalyst; and 2) preparing an N-heterocyclic compound represented by the following Chemical Formula 5-4 by hydrolysis-oxidation reaction of the N-heterocyclic compound represented by the Chemical Formula 1-4 prepared from step 1) above in the presence of $[Ru(p\text{-cymene})Cl_2]_2$ and deionized water:

[Chemical Formula 5-3]

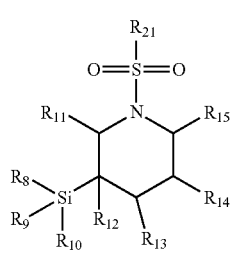

[Chemical Formula 2-3]

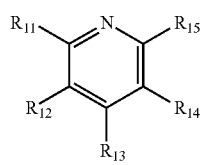

[Chemical Formula 3-1]

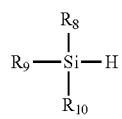

[Chemical Formula 1-3]

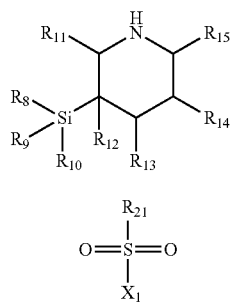

[Chemical Formula 4]

$$O=\underset{X_1}{\overset{R_{21}}{\underset{\|}{S}}}=O$$

[Chemical Formula 5-4]

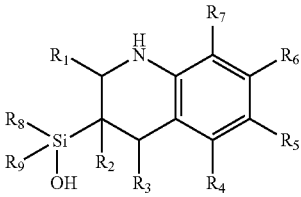

[Chemical Formula 2-1]

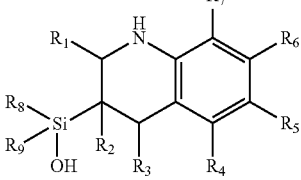

[Chemical Formula 3-2]

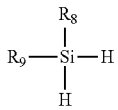

[Chemical Formula 1-4]

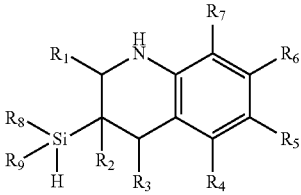

in Chemical Formulas 1-3, 2-3, 3-1, 4 and 5-3, $R_{11}$ to $R_{15}$ are each independently hydrogen, (C1-C10)alkyl, (C1-C10)alkoxy, (C6-C12)aryl, halogen or (C6-C12)aryloxy; and the alkyl, aryl and aryloxy of $R_{11}$ to $R_{15}$ may be further substituted with (C1-C10)alkyl;

$R_8$ and $R_9$ are each independently (C1-C10)alkyl or (C6-C12)aryl;

in Chemical Formulas 2-1, 3-2, 1-4 and 5-4, $R_1$ to $R_7$ are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12)alkenylene with or without a fused ring to form a monocyclic or polycyclic aromatic ring, and the alkyl, aryl and aryloxy of $R_1$ to $R_7$ may be further substituted with (C1-C10)alkyl; and $R_8$ and $R_9$ are each independently (C1-C10)alkyl or (C6-C12)aryl.

In the method of preparing the silylative-reduced N-heterocyclic compound according to an exemplary embodiment of the present invention, an N-heterocyclic compound represented by the following Chemical Formula 1-5 may be prepared by reacting a naphthyridine compound represented by the following Chemical Formula 2-4 with a silane compound represented by the following Chemical Formula 3-1, in the presence of the organoboron catalyst:

[Chemical Formula 1-5]

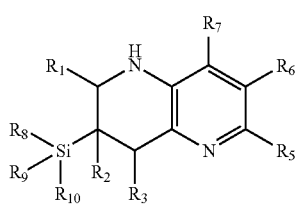

[Chemical Formula 2-4]

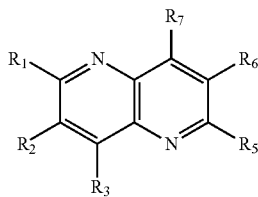

[Chemical Formula 3-1]

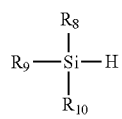

in Chemical Formulas 2-4, 3-1, and 1-5, $R_1$ to $R_3$ and $R_5$ to $R_7$ are each independently hydrogen, (C1-C10)alkyl, (C1-C10)alkoxy, (C6-C12)aryl, halogen or (C6-C12)aryloxy, and the alkyl, aryl and aryloxy of $R_1$ to $R_3$ and $R_5$ to $R_7$ may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

In the method of preparing the silylative-reduced N-heterocyclic compound according to an exemplary embodiment of the present invention, an N-heterocyclic compound represented by the following Chemical Formula 1-6 may be prepared by reacting a phenanthroline compound represented by the following Chemical Formula 2-5 with a silane compound represented by the following Chemical Formula 3-1, in the presence of the organoboron catalyst:

[Chemical Formula 1-6]

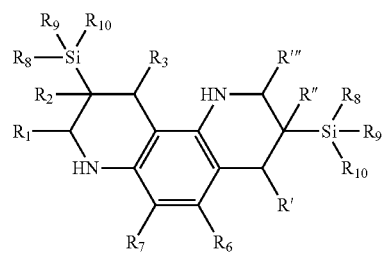

[Chemical Formula 2-5]

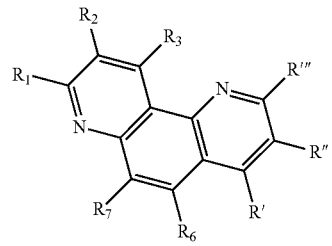

[Chemical Formula 3-1]

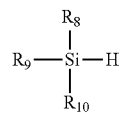

in Chemical Formulas 2-5, 3-1, and 1-6, $R_1$ to $R_3$, $R_6$, $R_7$, R', R" and R''' are each independently hydrogen, (C1-C10)alkyl, (C1-C10)alkoxy, (C6-C12)aryl, halogen or (C6-C12)aryloxy, and the alkyl, aryl and aryloxy of $R_1$ to $R_3$, $R_6$, $R_7$, R', R" and R''' may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

The method of preparing the silylative-reduced N-heterocyclic compound according to an exemplary embodiment of the present invention may include: 1) preparing an N-heterocyclic compound represented by the following Chemical Formula 1-7 by reacting a pyridine compound represented by the following Chemical Formula 2-3 with a silane compound represented by the following Chemical Formula 3-3, in the presence the an organoboron catalyst; and 2) preparing an N-heterocyclic compound represented by the following Chemical Formula 5-5 by reacting the N-heterocyclic compound represented by the Chemical Formula 1-7 prepared from step 1) above with a sulfonyl halide compound represented by the following Chemical Formula 4:

[Chemical Formula 5-5]

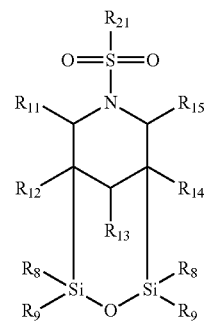

[Chemical Formula 2-3]

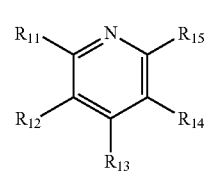

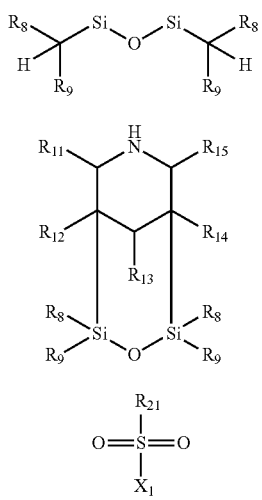

[Chemical Formula 3-3]

[Chemical Formula 1-7]

[Chemical Formula 4]

in Chemical Formulas 2-3, 3-3, 4, 1-7 and 5-5, $R_{11}$ to $R_{15}$ are each independently hydrogen, (C1-C10) alkyl, (C1-C10)alkoxy, (C6-C12)aryl, halogen or (C6-C12) aryloxy; and the alkyl, aryl and aryloxy of $R_{11}$ to $R_{15}$ may be further substituted with (C1-C10)alkyl;

$R_8$ and $R_9$ are each independently (C1-C10)alkyl or (C6-C12)aryl;

$R_{21}$ is (C3-C10)heteroaryl or (C6-C12)aryl, and the heteroaryl and aryl may be independently further substituted with at least one selected from (C1-C10)alkyl, halo(C1-C10) alkyl, (C6-C12)aryl, (C3-C10)cycloalkyl, cyano, halogen, and nitro; and $X_1$ is halogen.

According to the method of preparing the silylative-reduced N-heterocyclic compound of the present invention, the N-heterocyclic compound into which the silyl group is introduced at a beta position of the nitrogen atom by performing regioselective silylation of the N-heteroaromatic compound including a central ring having 5 to 20 carbon atoms and a sp² hybridized nitrogen atom while simultaneously reducing the N-resonance structure, using the silane compound which is the reducing agent, in the presence of the organoboron catalyst.

According to the method of preparing the silylative-reduced N-heterocyclic compound of the present invention, the silylative-reduced N-heterocyclic compound which is relatively difficult to be synthesized as a basic synthetic unit of a pharmaceutical product and an agrichemical product may be efficiently synthesized in a small number of steps, by performing regioselective introduction of the silyl group while simultaneously reducing the N-resonance structure, using the simple and relatively low-priced organoboron catalyst without including a metal and using the silane compound which is commercially available as the reducing agent, under a significantly mild condition.

Terms: [alkyl], [alkoxy], and other substituents including [alkyl[ part described in the present invention may include all linear or branched types. In addition, a term: [aryl] described in the present invention, which is an organic radical derived from aromatic hydrocarbon by removal of one hydrogen, may include single or fused ring system including ring atoms of 4 to 7, preferably, 5 or 6 in each ring, and may include a plurality of aryls linked by a single bond. Specific examples of the aryl may include phenyl, naphthyl, biphenyl, anthryl, fluorenyl, and the like, but the present invention is not limited thereto. Further, a term: [heteroaryl] described in the present invention, which means an aryl group containing 1 to 4 heteroatoms selected from B, N, O, S, P(=O), Si and P as an aromatic ring framework atom and carbon as the remaining aromatic ring framework atom, may include 5- to 6-membered monocyclic heteroaryl and polycyclic heteroaryl condensed with at least one benzene ring, and may be partially saturated. In addition, heteroaryl in the present invention may include one or more heteroaryls linked by a single bond.

The organoboron catalyst according to an exemplary embodiment of the present invention may be $B(C_6F_5)_3$ or $B(C_6F_5)_2Ar$, and the Ar may be (C6-C12)aryl.

The organoboron catalyst according to an exemplary embodiment of the present invention may be used at 0.1 to 5.0 mol %, preferably, 1.0 to 5.0 mol % based on 1 mol of the N-heteroaromatic compound. When the organoboron catalyst is used at the above-described range, high product selectivity may be obtained, and when the organoboron catalyst is used beyond the above-described range, an amount of side products may be relatively increased.

The silane compound according to an exemplary embodiment of the present invention may be used in amounts of 4 to 8 mol based on 1 mol of the N-heteroaromatic compound. When the silane compound is used at the above-described range, a rapid reaction rate and high yield may be obtained, and when the silane compound is used beyond the above-described range, yield of the product may be deteriorated (when the silane compound is used in amounts of less than 4 mol), and excessive amounts of silane (when the silane compound is used in amounts more of than 8 mol) may be wasted, which is not economical.

The silylative-reduction according to an exemplary embodiment of the present invention may be performed in the presence of an organic solvent, wherein the organic solvent is not limited as long as it does not react with the organoboron catalyst and the silane compound. Examples of the organic solvent may include chloroform, dichloromethane, toluene, chlorobenzene, benzene, hexane, dichloroethane, or mixed solvents thereof, and chloroform is preferably used in consideration of solubility of reactants, easiness of removal, and reaction efficiency.

A reaction temperature of the silylative-reduction according to an exemplary embodiment of the present invention is not limited as long as the temperature is generally used in organic synthesis, and the temperature may vary according to reaction time, amount of reaction materials and starting materials. The silylative-reduction may be performed at a reaction temperature of 23 to 100° C. in order to prevent deterioration of the reaction yield caused by an excessively increased reaction time or occurrence of side products.

The reaction time of the silylative-reduction according to an exemplary embodiment of the present invention may vary according to reaction materials, amounts of the reaction materials, kinds of solvents, and amounts of the solvents. The reaction time may be 10 mins to 24 hours. When the reaction time is over the above-described range, the side products may occur due to an excessively increased reaction time, such that reaction yield may be deteriorated.

When the reaction is completed, the solvent is distilled under reduced pressure, and a target material may be separated and purified by general methods such as column chromatography, recrystallization, and the like.

Advantageous Effects

According to the method of preparing a silylative-reduced N-heterocyclic compound of the present invention, the silylative-reduced N-heterocyclic compound which is relatively difficult to be synthesized as a basic synthetic unit of a pharmaceutical product and an agrichemical product may be efficiently synthesized in a small number of steps, by performing regioselective introduction of a silyl group while simultaneously reducing an N-resonance structure, using a simple and relatively low-priced organoboron catalyst without including a metal and using a silane compound which is commercially available as a reducing agent, under a significantly mild condition, unlike the existing method requiring a severe reaction condition, a multi-step reaction, and the use of a high-priced metal catalyst, and mass-production thereof is possible to be commercially available.

In addition, the silylative-reduced N-heterocyclic compound obtained by the present invention may have a silyl group to prepare a corresponding alcohol compound by an oxidation process. Further, the obtained corresponding alcohol compound may be substituted with other functional groups by known chemical reactions.

Therefore, the silylative-reduced N-heterocyclic compound prepared by the preparation method according to the present invention may be significantly and effectively applied as an intermediate and a synthetic unit in various fields such as alkaloids, pharmaceutical products and agrichemical products.

BEST MODE

Hereinafter, a configuration of the present invention will be described in detail with reference to examples. These examples are to help understanding of the present invention, and it will be obvious to those skilled in the art that the scope of the present invention is not construed to be limited to these examples.

Preparation Example: Preparation of Quinoline Derivative

[Preparation Example 1] Preparation of 8-isopropylquinoline

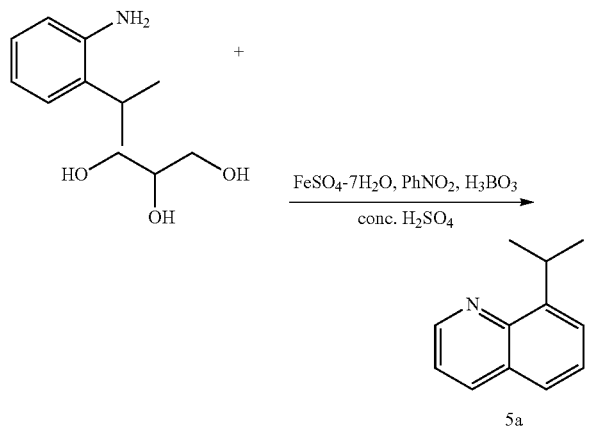

A boric acid (4.1 mmol, 1.0 eq) and glycerol (16 mmol, 4.0 eq) were added to a mixture of FeSO$_4$·7H$_2$O (0.49 mmol, 0.12 eq), 2-isopropyl aniline (4.1 mmol, 1.0 eq) and nitrobenzene (0.25 mL) at room temperature. The reaction mixture was cooled to 0° C., and a concentrated sulfuric acid (14 mmol, 3.3 eq) was slowly added thereto. Then, the reaction mixture was heated to 150° C., and stirred for 11 hours. After the stirring was completed, the reaction mixture was cooled to room temperature, and water (2 mL) and saturated NaHCO$_3$ aqueous solution (4 mL) were added thereto to thereby complete the reaction. Then, the reaction mixture was extracted with diethylether (10 mL×3), the obtained organic layer was washed with brine (30 mL×2), dried with anhydrous MgSO$_4$, followed by filtration and decompression concentration, and the residue was purified by silica gel column chromatography (EA/Hx=1/20) to obtain 8-isopropylquinoline (527 mg, 75%).

Colorless oil; $^1$H NMR (600 MHz, CDCl$_3$) δ 8.95 (dd, J=4.2, 1.8 Hz, 1H), 8.12 (dd, J=8.2, 1.7 Hz, 1H), 7.64 (ddd, J=12.0, 7.7, 1.4 Hz, 2H), 7.51 (dd, J=7.6, 7.6 Hz, 1H), 7.37 (dd, J=8.2, 4.1 Hz, 1H), 4.38 (sep, J=6.9 Hz, 1H), 1.41 (d, J=7.0 Hz, 6H); $^{13}$C NMR (150 MHz, CDCl$_3$) δ 149.1, 147.3, 146.1, 136.4, 128.3, 126.4, 125.5, 125.1, 120.7, 27.1, 23.5 (2C); IR (cm$^{-1}$) 2959, 2867, 1596, 1496, 1467, 1364, 1324, 1250, 1177, 1133, 1108, 1046, 1016, 828, 791, 755, 687; HRMS (EI): Calculated for C$_{12}$H$_{13}$N [M]$^+$: 171.1048. Found: 171.1047.

[Preparation Example 2] Preparation of 5-phenylquinoline

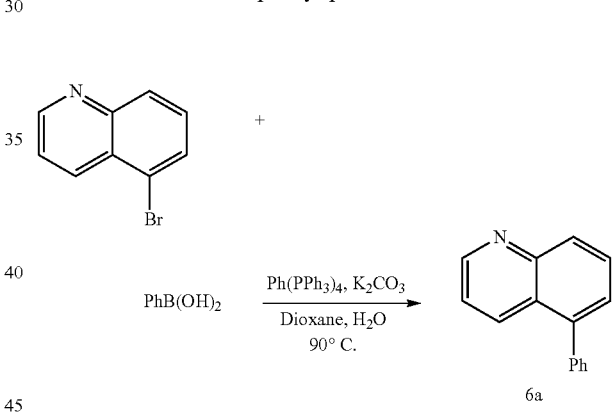

5-bromo-quinoline (2.0 mmol, 1.0 eq), phenyl boric acid (3.0 mmol, 1.5 eq), Pd(PPh$_3$)$_4$ (0.10 mmol, 5.0 mol %), K$_2$CO$_3$ (4.0 mmol, 2.0 eq), dioxane (8.0 mL) and water (2.0 mL) were mixed and refluxed at 90° C. After 12 hours, the reaction mixture was cooled at room temperature, and saturated NaHCO$_3$ aqueous solution (10 mL) was added thereto to thereby complete the reaction. Next, the reaction mixture was extracted with ethyl acetate (10 mL×3), the obtained organic layer was washed with brine (20 mL×2), dried with anhydrous MgSO$_4$, followed by filtration and decompression concentration, and the residue was purified by silica gel column chromatography (EA/Hx=1/10) to obtain 5-phenylquinoline (386 mg, 99%).

Bright yellow solid; $^1$H NMR (600 MHz, CDCl$_3$) δ 8.93 (dd, J=4.1, 1.7 Hz, 1H), 8.29-8.23 (m, 1H), 8.19-8.09 (m, 1H), 7.76 (dd, J=8.5, 7.0 Hz, 1H), 7.53-7.49 (m, 3H), 7.48-7.44 (m, 3H), 7.35 (dd, J=8.6, 4.1 Hz, 1H); $^{13}$C NMR (150 MHz, CDCl$_3$) δ 150.2, 148.5, 140.5, 139.4, 134.3, 130.0 (2C), 129.0, 128.9, 128.4 (2C), 127.6, 127.2, 126.7, 121.0.

[Preparation Example 3] Preparation of 7-phenylquinoline

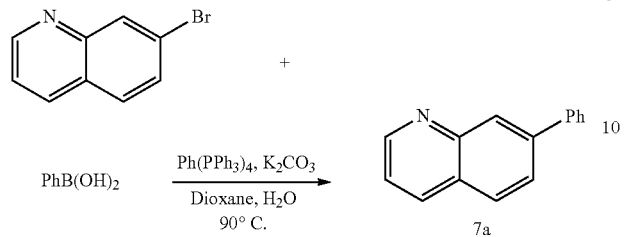

7-bromo-quinoline (2.0 mmol, 1.0 eq), phenyl boric acid (3.0 mmol, 1.5 eq), Pd(PPh$_3$)$_4$ (0.10 mmol, 5.0 mol %), K$_2$CO$_3$ (4.0 mmol, 2.0 eq), dioxane (8.0 mL) and water (2.0 mL) were mixed and refluxed at 90° C. After 14 hours, the reaction mixture was cooled at room temperature, and saturated NaHCO$_3$ aqueous solution (10 mL) was added thereto to thereby complete the reaction. Next, the reaction mixture was extracted with ethyl acetate (10 mL×3), the obtained organic layer was washed with brine (20 mL×2), dried with anhydrous MgSO$_4$, followed by filtration and decompression concentration, and the residue was purified by silica gel column chromatography (EA/Hx=1/10) to obtain 7-phenylquinoline (386 mg, 94%).

Bright yellow oil; $^1$H NMR (600 MHz, CDCl$_3$) δ 8.95 (dd, J=4.2, 1.7 Hz, 1H), 8.35 (s, 1H), 8.18 (d, J=8.3 Hz, 1H), 7.89 (d, J=8.5 Hz, 1H), 7.83 (dd, J=8.5, 1.8 Hz, 1H), 7.81-7.68 (m, 2H), 7.51 (dd, J=8.3, 7.1 Hz, 2H), 7.46-7.34 (m, 2H); $^{13}$C NMR (150 MHz, CDCl$_3$) δ 150.8, 148.5, 142.3, 140.3, 135.8, 129.0 (2C), 128.2, 127.9, 127.5 (2C), 127.4, 127.1, 126.3, 121.0; IR (cm$^{-1}$) 3035, 1736, 1619, 1488, 1427, 942, 891, 836, 753, 693, 566, 477; HRMS (EI): Calculated for C$_{15}$H$_{11}$N [M]$^+$: 205.0891. Found: 205.0889.

[Preparation Example 4] Preparation of 6-(p-tolyloxy)quinoline

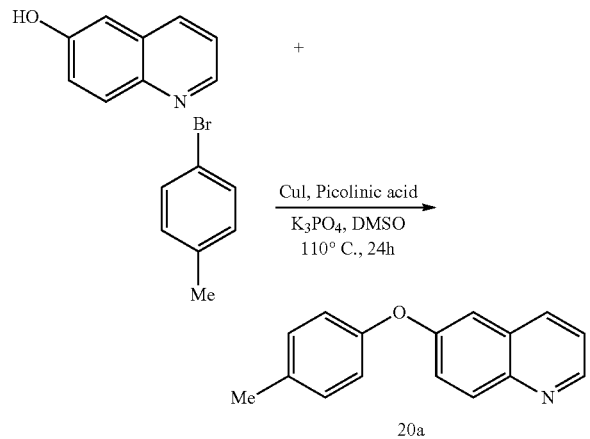

6-hydroxyquinoline (1.2 mmol, 1.2 eq), picolinic acid (0.20 mmol, 20 mol %), CuI (0.10 mmol, 10 mol %), K$_3$PO$_4$ (2.0 mmol, 2.0 eq), 1-bromo-4-methylbenzene (1.0 mmol, 1.0 eq), and DMSO (dimethylsulfoxide, 2.0 mL) were mixed and refluxed at 110° C. After 24 hours, the reaction mixture was cooled at room temperature, and water (1 mL) was added thereto to thereby complete the reaction. Next, the reaction mixture was extracted with ethyl acetate (10 mL×2), the obtained organic layer was washed with saturated ammonium chloride aqueous solution (20 mL×2), dried with anhydrous MgSO$_4$, followed by filtration and decompression concentration, and the residue was purified by silica gel column chromatography (EA/Hx=1/4) to obtain 6-(p-tolyloxy)quinoline (202 mg, 86%).

Colorless oil; $^1$H NMR (600 MHz, CDCl$_3$) δ 8.77 (dd, J=4.2, 1.7 Hz, 1H), 8.06 (d, J=9.1 Hz, 1H), 7.96-7.84 (m, 1H), 7.45 (dd, J=9.1, 2.7 Hz, 1H), 7.28 (dd, J=8.3, 4.2 Hz, 1H), 7.19-7.09 (m, 3H), 6.97 (d, J=8.4 Hz, 2H), 2.33 (s, 3H); $^{13}$C NMR (150 MHz, CDCl$_3$) δ 156.0, 153.8, 148.6, 144.8, 134.9, 133.6, 131.1, 130.3 (2C), 128.9, 122.8, 121.2, 119.6 (2C), 111.9, 20.6; IR (cm$^{-1}$) 3023, 2954, 1595, 1494, 1462, 1374, 1322, 960, 825; HRMS (EI): Calculated for C$_{16}$H$_{13}$NO [M]$^+$: 235.0997. found: 235.0998.

Example I: Preparation of Silylative-Reduced Tetrahydroquinoline Compound (Chemical Formula 1-1)

[Example 1] Preparation of 3-(diethylsilyl)-1,2,3,4-tetrahydroquinoline (1b)

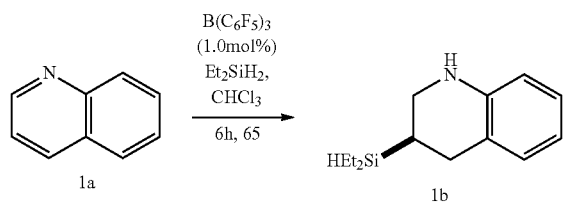

B(C$_6$F$_5$)$_3$ (0.0050 mmol, 1.0 mol %) was dissolved in chloroform (0.50 mL) in a 2.5 mL reaction vial, then diethylsilane (2.0 mmol, 4.0 eq) and quinoline (1a, 0.50 mmol, 1.0 eq) were sequentially added thereto. The reaction mixture was stirred at 65° C. for 6 hours, cooled to room temperature, and filtrated by passing through a silica gel pad with dichloromethane (15 mL) and methanol (2 mL). After decompression concentration of the filtrate, the residue was purified by silica gel column chromatography (EA/Hx=5/95) to obtain 3-(diethylsilyl)-1,2,3,4-tetrahydroquinoline (1b) (yield: 86%).

Colorless oil; $^1$H NMR (600 MHz, CDCl$_3$) δ 7.11-6.87 (m, 2H), 6.61 (ddd, J=7.6, 1.3, 1.3 Hz, 1H), 6.47 (d, J=7.9 Hz, 1H), 3.89 (br, 1H), 3.63 (d, J=3.1 Hz, 1H), 3.39 (ddd, J=11.6, 3.4, 1.7 Hz, 1H), 3.23 (t, J=11.4 Hz, 1H), 2.87-2.64 (m, 2H), 1.46 (tdd, J=11.4, 5.7, 2.9 Hz, 1H), 1.04 (td, J=7.9, 1.4 Hz, 6H), 0.69 (tdd, J=11.3, 6.3, 3.3 Hz, 4H); $^{13}$C NMR (150 MHz, CDCl$_3$) δ 144.5, 129.0, 126.7, 121.8, 116.9, 114.3, 44.0, 29.1, 17.7, 8.3 (2C), 1.3, 1.2; $^{29}$Si NMR (120 MHz, CDCl$_3$) δ 0.15; IR (cm$^{-1}$) 3403, 2951, 2828, 2093, 1604, 1502, 1262, 1246, 1008, 803, 742; HRMS (EI): Calculated for C$_{13}$H$_{21}$NSi [M]$^+$: 219.1443. Found: 219.1442.

[Example 2] Preparation of 3-(diethylsilyl)-6-methyl-1,2,3,4-tetrahydroquinoline (2b)

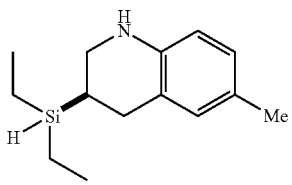 [SMILES: CC[SiH](CC)[C@H]1CNc2ccc(C)cc2C1]

3-(diethylsilyl)-6-methyl-1,2,3,4-tetrahydroquinoline (2b) (yield: 85%) was obtained by the same method as Example 1 above except for using 6-methylquinoline (2a) instead of quinoline (1a).

Bright yellow oil; $^1$H NMR (600 MHz, CDCl$_3$) δ 6.94-6.88 (m, 2H), 6.51 (d, J=8.0 Hz, 1H), 3.84-3.76 (m, 2H), 3.46 (ddd, J=11.5, 2.2, 2.2 Hz, 1H), 3.30 (t, J=11.4 Hz, 1H), 2.88-2.83 (m, 2H), 2.35 (s, 3H), 1.58 (dtd, J=10.9, 6.9, 3.2 Hz, 1H), 1.18 (td, J=7.9, 1.3 Hz, 6H), 0.82 (qt, J=8.0, 3.3 Hz, 4H); $^{13}$C NMR (150 MHz, CDCl$_3$) δ 142.1, 129.4, 127.1, 125.8, 121.7, 114.4, 44.1, 29.0, 20.3, 17.8, 8.3 (2C), 1.2, 1.1; $^{29}$Si NMR (120 MHz, CDCl$_3$) δ 0.43; IR (cm$^{-1}$) 3391, 2951, 2872, 2093, 1618, 1510, 1266, 1249, 1232, 1009, 802; HRMS (EI): Calculated for C$_{14}$H$_{23}$NSi [M]$^+$: 233.1600. Found: 233.1601.

[Example 3] Preparation of 3-(diethylsilyl)-7-methyl-1,2,3,4-tetrahydroquinoline (3b)

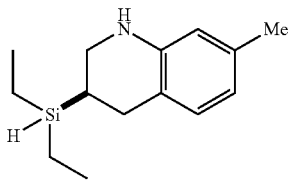 [SMILES: CC[SiH](CC)[C@H]1CNc2cc(C)ccc2C1]

3-(diethylsilyl)-7-methyl-1,2,3,4-tetrahydroquinoline (3b) (yield: 81%) was obtained by the same method as Example 1 above except for using 7-methylquinoline (3a) instead of quinoline (1a).

Yellow oil; $^1$H NMR (600 MHz, CDCl$_3$) δ 6.86 (dd, J=7.9, 2.0 Hz, 1H), 6.47 (dd, J=7.7, 1.9 Hz, 1H), 6.33 (s, 1H), 3.60 (br, 1H), 3.71-3.58 (m, 1H), 3.45-3.29 (m, 1H), 3.28-3.14 (m, 1H), 2.84-2.67 (m, 2H), 2.25 (s, 3H), 1.47 (ddt, J=11.4, 5.6, 2.9 Hz, 1H), 1.06 (td, J=7.9, 2.4 Hz, 6H), 0.82-0.57 (m, 4H); $^{13}$C NMR (150 MHz, CDCl$_3$) δ 144.4, 136.3, 128.8, 118.9, 117.8, 114.8, 44.0, 28.7, 21.1, 17.9, 8.3 (2C), 1.4, 1.2; $^{29}$Si NMR (120 MHz, CDCl$_3$) δ 0.37; IR (cm$^{-1}$): 3417, 2952, 2873, 2097, 1600, 1501, 1258, 1228, 806, 752; HRMS (EI): Calculated for C$_{14}$H$_{23}$NSi [M]$^+$: 233.1600. Found: 233.1601.

[Example 4] Preparation of 3-(diethylsilyl)-8-methyl-1,2,3,4-tetrahydroquinoline (4b)

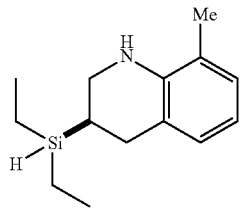

3-(diethylsilyl)-8-methyl-1,2,3,4-tetrahydroquinoline (4b) (yield: 96%) was obtained by the same method as Example 1 above except for using 8-methylquinoline (4a) instead of quinoline (1a).

Bright yellow oil; $^1$H NMR (400 MHz, CDCl$_3$) δ 7.10-6.80 (m, 2H), 6.68 (dd, J=7.4, 7.4 Hz, 1H), 3.77 (q, J=3.1 Hz, 1H), 3.73 (br, 1H) 3.69-3.51 (m, 1H), 3.38 (t, J=11.5 Hz, 1H), 3.06-2.67 (m, 2H), 2.19 (s, 3H), 1.76-1.38 (m, 1H), 1.16 (t, J=7.9 Hz, 6H), 0.90-0.68 (m, 4H); $^{13}$C NMR (100 MHz, CDCl$_3$) δ 142.4, 127.7, 126.8, 121.20, 121.19, 116.2, 44.3, 29.4, 17.8, 17.0, 8.35, 8.33, 1.3, 1.1; $^{29}$Si NMR (120 MHz, CDCl$_3$) δ 0.43; IR (cm$^{-1}$): 3422, 2951, 2872, 2092, 1598, 1492, 1264, 1247, 1223, 1008, 803, 753; HRMS (EI): Calculated for C$_{14}$H$_{23}$NSi [M]$^+$: 233.1600. Found: 233.1599.

[Example 5] Preparation of 3-(diethylsilyl)-8-isopropyl-1,2,3,4-tetrahydroquinoline (5b)

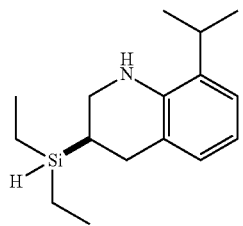

3-(diethylsilyl)-8-isopropyl-1,2,3,4-tetrahydroquinoline (5b) (yield: 90%) was obtained by the same method as Example 1 above except for using 8-isopropylquinoline (5a) instead of quinoline (1a).

Colorless oil; $^1$H NMR (600 MHz, CDCl$_3$) δ 7.07-6.97 (m, 1H), 6.86 (dd, J=7.5, 1.4 Hz, 1H), 6.66 (d, J=7.5, 7.5 Hz, 1H), 3.93 (s, 1H), 3.67 (q, J=3.1 Hz, 1H), 3.56-3.50 (m, 1H), 3.30 (t, J=11.5 Hz, 1H), 2.95-2.75 (m, 3H), 1.56-1.43 (m, 1H), 1.27 (d, J=6.8 Hz, 6H), 1.06 (t, J=7.9 Hz, 6H), 0.77-0.64 (m, 4H); $^{13}$C NMR (150 MHz, CDCl$_3$) δ 141.2, 131.6, 126.8, 122.7, 121.7, 116.6, 44.5, 29.9, 26.9, 22.5, 22.2, 17.6, 8.40, 8.37, 1.4, 1.2; $^{29}$Si NMR (120 MHz, CDCl$_3$) δ 0.39; IR (cm$^{-1}$) 2954, 2873, 2093, 1596, 1491, 1459, 1349, 1261, 1010, 967, 804, 740; HRMS (EI): Calculated for C$_{16}$H$_{27}$NSi [M]$^+$: 261.1913. Found: 261.1909.

[Example 6] Preparation of 3-(diethylsilyl)-5-phenyl-1,2,3,4-tetrahydroquinoline (6b)

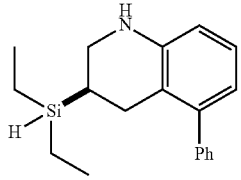

3-(diethylsilyl)-5-phenyl-1,2,3,4-tetrahydroquinoline (6b) (yield: 70%) was obtained by the same method as Example 1 above except for using 5-phenylquinoline (6a) instead of quinoline (1a).

Colorless oil; $^1$H NMR (600 MHz, CDCl$_3$) δ 7.38 (dd, J=8.6, 6.7 Hz, 2H), 7.35-7.28 (m, 3H), 7.01 (t, J=7.7 Hz, 1H), 6.60-6.53 (m, 1H), 6.48 (dd, J=8.2, 1.3 Hz, 1H), 3.58-3.47 (m, 1H), 3.43-3.35 (m, 1H), 3.24 (t, J=11.3 Hz, 1H), 2.69-2.61 (m, 1H), 2.55 (dd, J=16.5, 11.7 Hz, 1H), 1.31 (d, J=3.6 Hz, 1H), 0.94 (dtd, J=14.5, 7.9, 1.2 Hz, 6H), 0.70-0.40 (m, 4H); $^{13}$C NMR (150 MHz, CDCl$_3$) δ 144.6, 142.2, 141.8, 129.1 (2C), 127.8 (2C), 126.5, 126.3, 119.3, 118.7, 113.5, 43.9, 27.7, 17.7, 8.31, 8.29, 1.3, 1.2; $^{29}$Si NMR (120 MHz, CDCl$_3$) δ 0.39; IR (cm$^{-1}$): 3405, 2952, 2873, 2096, 1588, 1487, 1459, 1257, 1011, 810, 759; HRMS (EI): Calculated C$_{19}$H$_{25}$NSi [M]$^+$: 295.1756. Found: 295.1754.

[Example 7] Preparation of 3-(diethylsilyl)-7-phenyl-1,2,3,4-tetrahydroquinoline (7b)

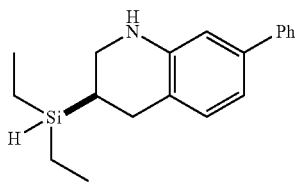 [SMILES: CC[SiH](CC)[C@H]1CNc2cc(-c3ccccc3)ccc2C1]

3-(diethylsilyl)-7-phenyl-1,2,3,4-tetrahydroquinoline (7b) (yield: 61%) was obtained by the same method as Example 1 above except for using 7-phenylquinoline (7a) instead of quinoline (1a).

White solid; m.p. 55-57° C.; $^1$H NMR (600 MHz, CDCl$_3$) δ 7.56 (dt, J=7.8, 1.7 Hz, 2H), 7.41 (td, J=7.7, 2.2 Hz, 2H), 7.32 (tt, J=7.7, 1.4 Hz, 1H), 7.02 (dd, J=7.7, 2.3 Hz, 1H), 6.86 (dt, J=7.7, 2.1 Hz, 1H), 6.71 (t, J=2.0 Hz, 1H), 3.71-3.63 (m, 1H), 3.51-3.38 (m, 1H), 3.28 (td, J=11.4, 2.3 Hz, 1H), 2.90-2.71 (m, 2H), 1.51 (dtd, J=8.9, 5.9, 3.0 Hz, 1H), 1.14-1.00 (m, 6H), 0.72 (dq, J=8.4, 2.7 Hz, 4H); $^{13}$C NMR (150 MHz, CDCl$_3$) δ 144.8, 141.6, 140.0, 129.4, 128.5 (2C), 126.9 (2C), 126.8, 121.2, 116.0, 112.9, 44.1, 28.9, 17.8, 8.4 (2C), 1.4, 1.2; $^{29}$Si NMR (120 MHz, CDCl$_3$) δ 0.39; IR (cm$^{-1}$) 2951, 2908, 2872, 2090, 1609, 1565, 1484, 1386, 1319, 1288, 1260, 1226, 1008, 804, 757, 695; HRMS (EI): Calculated for C$_{19}$H$_{25}$NSi [M]$^+$: 295.1756. Found: 295.1754.

[Example 8] Preparation of 3-(diethylsilyl)-4-methyl-1,2,3,4-tetrahydroquinoline (8b)

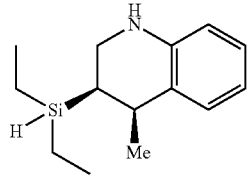 [SMILES: CC[SiH](CC)[C@H]1CNc2ccccc2[C@H]1C]

3-(diethylsilyl)-4-methyl-1,2,3,4-tetrahydroquinoline (8b) (yield: 95%) was obtained by the same method as Example 1 above except for using 4-methylquinoline (8a) instead of quinoline (1a) and stirring for 24 hours.

Yellow oil; $^1$H NMR (400 MHz, CDCl$_3$) δ 7.13-7.06 (m, 1H), 7.00 (dddd, J=7.9, 7.2, 1.5, 0.6 Hz, 1H), 6.69 (td, J=7.4, 1.3 Hz, 1H), 6.51 (dd, J=8.0, 1.3 Hz, 1H), 3.63 (td, J=3.4, 2.7 Hz, 1H), 3.52 (dd, J=11.3, 3.6 Hz, 1H), 3.25 (ddd, J=11.3, 6.0, 0.7 Hz, 1H), 2.96 (dd, J=7.0, 4.7 Hz, 1H), 1.39 (d, J=7.0 Hz, 3H), 1.28-1.18 (m, 1H), 1.08-0.91 (m, 6H), 0.72-0.52 (m, 4H); $^{13}$C NMR (100 MHz, CDCl$_3$) δ 144.6, 128.9, 126.8, 126.5, 117.2, 114.4, 40.5, 32.1, 25.2, 25.1, 8.5, 8.4, 1.9, 1.7; $^{29}$Si NMR (120 MHz, CDCl$_3$) δ 0.49; IR (cm$^{-1}$): 3392, 2953, 2872, 2092, 1783, 1606, 1499, 1260, 1228, 1014, 814, 744; HRMS (EI): Calculated for C$_{14}$H$_{23}$NSi [M]$^+$: 233.1600. Found: 233.1603.

[Example 9] Preparation of 3-(diethylsilyl)-3-methyl-1,2,3,4-tetrahydroquinoline (9b)

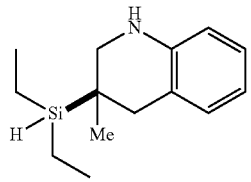 [SMILES: CC[SiH](CC)[C@@]1(C)CNc2ccccc2C1]

3-(diethylsilyl)-3-methyl-1,2,3,4-tetrahydroquinoline (9b) (yield: 92%) was obtained by the same method as Example 1 above except for using 3-methylquinoline (9a) instead of quinoline (1a) and stirring for 24 hours.

Colorless oil; $^1$H NMR (600 MHz, CDCl$_3$) δ 7.00 (ddd, J=7.8, 7.0, 1.5 Hz, 1H), 6.96 (dt, J=7.5, 1.2 Hz, 1H), 6.64 (td, J=7.4, 1.2 Hz, 1H), 6.49 (dd, J=8.0, 1.2 Hz, 1H), 3.85 (br, 1H), 3.61-3.47 (m, 1H), 3.32 (dd, J=11.2, 1.1 Hz, 1H), 2.99 (dd, J=11.3, 1.6 Hz, 1H), 2.91 (d, J=16.1 Hz, 1H), 2.48 (d, J=16.1 Hz, 1H), 1.30-0.91 (m, 9H), 0.81-0.45 (m, 4H); $^{13}$C NMR (150 MHz, CDCl$_3$) δ 144.1, 129.7, 126.5, 120.0, 116.9, 113.7, 49.9, 36.9, 20.9, 19.3, 8.9, 8.8, 0.8, 0.6; $^{29}$Si NMR (120 MHz, CDCl$_3$) δ 6.71; IR (cm$^{-1}$) 3397, 2951, 2828, 2092, 1617, 1487, 1261, 1232, 1010, 787; HRMS (EI): Calculated for C$_{14}$H$_{23}$NSi [M]$^+$: 233.1600. Found: 233.1598.

[Example 10] Preparation of 5-chloro-3-(diethylsilyl)-1,2,3,4-tetrahydroquinoline (10b)

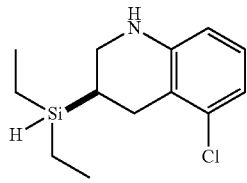 [SMILES: CC[SiH](CC)[C@H]1CNc2cccc(Cl)c2C1]

5-chloro-3-(diethylsilyl)-1,2,3,4-tetrahydroquinoline (10b) (yield: 94%) was obtained by the same method as Example 1 above except for using 5-chloroquinoline (10a) instead of quinoline (1a).

Yellow oil; $^1$H NMR (600 MHz, CDCl$_3$) δ 6.91 (t, J=7.9 Hz, 1H), 6.72 (dd, J=8.0, 1.3 Hz, 1H), 6.38 (d, J=8.0 Hz, 1H), 4.01 (s, 1H), 3.82-3.56 (m, 1H), 3.37 (ddd, J=11.5, 3.4, 1.9 Hz, 1H), 3.19 (t, J=11.4 Hz, 1H), 3.03 (ddd, J=17.1, 5.1, 1.9 Hz, 1H), 2.61 (dd, J=17.0, 12.0 Hz, 1H), 1.45 (dt, J=5.8, 3.4 Hz, 1H), 1.10 (tdt, J=8.0, 2.6, 1.3 Hz, 6H), 0.83-0.51 (m, 4H); $^{13}$C NMR (150 MHz, CDCl$_3$) δ 146.1, 134.3, 126.9, 119.3, 117.3, 112.5, 43.3, 26.6, 17.3, 8.3 (2C), 1.3, 1.1; $^{29}$Si NMR (120 MHz, CDCl$_3$) δ 0.52; IR (cm$^{-1}$): 3413, 2952, 2873, 2095, 1596, 1487, 1260, 1233, 1009, 807, 762; HRMS (EI): Calculated for C$_{13}$H$_{20}$ClNSi [M]$^+$: 253.1054. Found: 253.1051.

[Example 11] Preparation of 5-bromo-3-(diethylsilyl)-1,2,3,4-tetrahydroquinoline (11b)

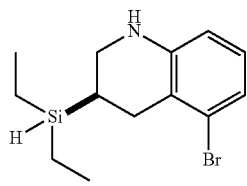 [SMILES: CC[SiH](CC)[C@H]1CNc2cccc(Br)c2C1]

5-bromo-3-(diethylsilyl)-1,2,3,4-tetrahydroquinoline (11b) (yield: 85%) was obtained by the same method as Example 1 above except for using 5-bromoquinoline (11a) instead of quinoline (1a).

Colorless oil; $^1$H NMR (600 MHz, CDCl$_3$) δ 6.87 (dd, J=7.8, 1.2 Hz, 1H), 6.82 (t, J=7.9 Hz, 1H), 6.41 (dd, J=8.0, 1.2 Hz, 1H), 4.01 (s, 1H), 3.68 (q, J=3.1 Hz, 1H), 3.35 (ddd, J=11.5, 3.5, 1.9 Hz, 1H), 3.17 (t, J=11.4 Hz, 1H), 2.96 (ddd, J=17.0, 5.0, 1.9 Hz, 1H), 2.69-2.49 (m, 1H), 1.50-1.35 (m, 1H), 1.06 (td, J=7.9, 3.6 Hz, 6H), 0.72 (dddd, J=12.8, 8.0, 7.0, 3.3 Hz, 4H); $^{13}$C NMR (150 MHz, CDCl$_3$) δ 146.3, 127.5, 125.6, 121.0, 120.6, 113.3, 43.5, 29.7, 17.8, 8.4, 8.3, 1.4, 1.2; $^{29}$Si NMR (120 MHz, CDCl$_3$) δ 0.38; IR (cm$^{-1}$) 2952, 2873, 2093, 1593, 1486, 1457, 1344, 1312, 1260, 1230, 1193, 805, 759; HRMS (EI): Calculated for C$_{13}$H$_{20}$BrNSi [M]$^+$: 297.0548. Found: 297.0551.

[Example 12] Preparation of 3-(diethylsilyl)-6-fluoro-1,2,3,4-tetrahydroquinoline (12b)

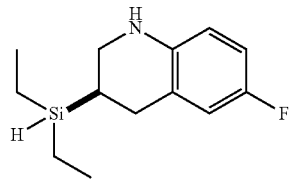 [SMILES: CC[SiH](CC)[C@H]1CNc2ccc(F)cc2C1]

3-(diethylsilyl)-6-fluoro-1,2,3,4-tetrahydroquinoline (12b) (yield: 73%) was obtained by the same method as Example 1 above except for using 6-fluoroquinoline (12a) instead of quinoline (1a).

Colorless oil; $^1$H NMR (600 MHz, CDCl$_3$) δ 6.75-6.64 (m, 2H), 6.40 (dd, J=8.4, 4.8 Hz, 1H), 3.65 (q, J=3.1 Hz, 1H), 3.37 (ddd, J=11.4, 3.4, 1.6 Hz, 1H), 3.19 (t, J=11.4 Hz, 1H), 2.81-2.63 (m, 2H), 1.47-1.34 (m, 1H), 1.05 (td, J=7.9, 1.4 Hz, 6H), 0.80-0.53 (m, 4H); $^{13}$C NMR (150 MHz, CDCl$_3$) δ 155.4 (d, J=234.9 Hz), 140.7 (d, J=1.8 Hz), 123.1 (d, J=6.3 Hz), 115.2 (d, J=21.4 Hz), 115.0 (d, J=7.5 Hz), 113.2 (d, J=22.5 Hz), 44.2, 29.2, 17.6, 8.3 (2C), 1.3, 1.2; $^{19}$F NMR (564 MHz, CDCl$_3$) δ −128.1 (td, J=8.8, 4.9 Hz); $^{29}$Si NMR (120 MHz, CDCl$_3$) δ 0.39; IR (cm$^{-1}$) 2953, 2910, 2874, 2095, 1503, 1348, 1243, 1221, 1221, 1140, 850, 800; HRMS (EI): Calculated for C$_{13}$H$_{20}$FNSi [M]$^+$: 237.1349. Found: 237.1349.

[Example 13] Preparation of 6-bromo-3-(diethylsilyl)-1,2,3,4-tetrahydroquinoline (13b)

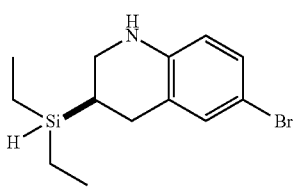 [SMILES: CC[SiH](CC)[C@H]1CNc2ccc(Br)cc2C1]

6-bromo-3-(diethylsilyl)-1,2,3,4-tetrahydroquinoline (13b) (yield: 94%) was obtained by the same method as Example 1 above except for using 6-bromoquinoline (13a) instead of quinoline (1a).

Colorless oil; $^1$H NMR (600 MHz, CDCl$_3$) δ 7.04 (d, J=9.1 Hz, 2H), 6.33 (dd, J=8.1, 1.6 Hz, 1H), 3.87 (br, 1H), 3.65 (q, J=3.2, 2.8 Hz, 1H), 3.49-3.28 (m, 1H), 3.20 (td, J=11.4, 1.6 Hz, 1H), 2.72 (qd, J=16.3, 8.1 Hz, 2H), 1.40 (td, J=4.7, 2.2 Hz, 1H), 1.05 (tt, J=7.9, 1.2 Hz, 6H), 0.70 (dt, J=7.7, 2.6 Hz, 4H); $^{13}$C NMR (150 MHz, CDCl$_3$) δ 143.4, 131.3, 129.2, 123.7, 115.5, 108.0, 43.8, 29.0, 17.2, 8.3 (2C), 1.3, 1.1; $^{29}$Si NMR (120 MHz, CDCl$_3$) δ 0.32; IR (cm$^{-1}$) 3411, 2950, 2872, 2089, 1598, 1491, 1261, 1243, 1229, 1004, 800, 705; HRMS (EI): Calculated for C$_{13}$H$_{20}$BrNSi [M]$^+$: 297.0548. Found: 297.0551.

[Example 14] Preparation of 7-chloro-3-(diethylsilyl)-1,2,3,4-tetrahydroquinoline (14b)

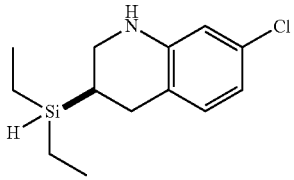 [SMILES: CC[SiH](CC)[C@H]1CNc2cc(Cl)ccc2C1]

7-chloro-3-(diethylsilyl)-1,2,3,4-tetrahydroquinoline (14b) (yield: 87%) was obtained by the same method as Example 1 above except for using 7-chloroquinoline (14a) instead of quinoline (1a) and stirring at 23° C. for 6 hours.

Bright yellow oil; $^1$H NMR (600 MHz, CDCl$_3$) δ 6.81 (d, J=8.0 Hz, 1H), 6.53 (dd, J=8.0, 2.1 Hz, 1H), 6.42 (d, J=2.1 Hz, 1H), 3.89 (br, 1H), 3.62 (q, J=3.1 Hz, 1H), 3.37 (ddd, J=11.7, 3.6, 2.0 Hz, 1H), 3.19 (t, J=11.4 Hz, 1H), 2.86-2.47 (m, 2H), 1.39 (dt, J=4.6, 3.3 Hz, 1H), 1.02 (td, J=7.9, 1.2 Hz, 6H), 0.67 (dd, J=7.7, 3.6 Hz, 4H); $^{13}$C NMR (150 MHz, CDCl$_3$) δ 145.4, 131.8, 129.9, 120.0, 116.4, 113.4, 43.7, 28.7, 17.3, 8.3 (2C), 1.3, 1.2; $^{29}$Si NMR (120 MHz, CDCl$_3$) δ 0.36; IR (cm$^{-1}$): 3410, 2953, 2873, 2098, 1600, 1497, 1259, 1238, 1080, 882, 784; HRMS (EI): Calculated for C$_{13}$H$_{20}$ClNSi [M]$^+$: 253.1054. Found: 253.1053.

[Example 15] Preparation of 8-chloro-3-(diethylsilyl)-1,2,3,4-tetrahydroquinoline (15b)

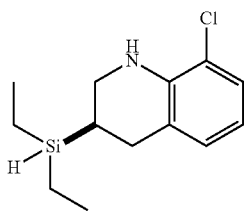 [SMILES: CC[SiH](CC)[C@H]1CNc2c(Cl)cccc2C1]

8-chloro-3-(diethylsilyl)-1,2,3,4-tetrahydroquinoline (15b) (yield: 94%) was obtained by the same method as Example 1 above except for using 8-chloroquinoline (15a) instead of quinoline (1a) and stirring at 23° C. for 6 hours.

Colorless oil; $^1$H NMR (600 MHz, CDCl$_3$) δ 7.11-6.93 (m, 1H), 6.89-6.68 (m, 1H), 6.51 (t, J=7.7 Hz, 1H), 4.49 (br, 1H), 3.64 (q, J=3.1 Hz, 1H), 3.51 (ddd, J=11.7, 3.6, 2.0 Hz, 1H), 3.28 (t, J=11.6 Hz, 1H), 3.04-2.56 (m, 2H), 1.47-1.36 (m, 1H), 1.09-0.93 (m, 6H), 0.74-0.64 (m, 4H); $^{13}$C NMR (150 MHz, CDCl$_3$) δ 140.5, 127.1, 126.7, 123.1, 118.1, 116.1, 43.8, 29.4, 17.2, 8.3, 1.3, 1.2; $^{29}$Si NMR (80 MHz, CDCl$_3$) δ 0.37; IR (cm-1): 3421, 2953, 2092, 1600, 1491, 1332, 1261, 1229, 1051, 801, 784; HRMS (EI): Calculated for C$_{13}$H$_{20}$ClNSi [M]$^+$: 253.1054. Found: 253.1053.

[Example 16] Preparation of 8-bromo-3-(diethylsilyl)-1,2,3,4-tetrahydroquinoline (16b)

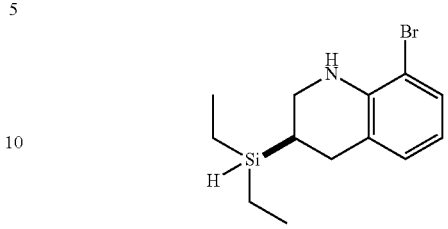

8-bromo-3-(diethylsilyl)-1,2,3,4-tetrahydroquinoline (16b) (yield: 91%) was obtained by the same method as Example 1 above except for using 8-bromoquinoline (16a) instead of quinoline (1a) and stirring at 23° C. for 10 mins.

Colorless oil; $^1$H NMR (400 MHz, CDCl$_3$) δ 7.27 (dt, J=7.8, 1.3 Hz, 1H), 6.92 (dt, J=7.4, 1.2 Hz, 1H), 6.49 (dd, J=8.4, 6.9 Hz, 1H), 4.56 (br, 1H), 3.68 (d, J=3.0 Hz, 1H), 3.60-3.47 (m, 1H), 3.32 (t, J=11.6 Hz, 1H), 2.91-2.59 (m, 2H), 1.45 (dd, J=3.1, 2.0 Hz, 1H), 1.08 (td, J=7.8, 1.1 Hz, 6H), 0.77-0.61 (m, 4H); $^{13}$C NMR (100 MHz, CDCl$_3$) δ 141.4, 129.9, 127.8, 123.3, 116.7, 108.7, 44.1, 29.6, 17.1, 8.3 (2C), 1.3, 1.1; $^{29}$Si NMR (120 MHz, CDCl$_3$) δ 0.27; IR (cm$^{-1}$): 3413, 2951, 2872, 2094, 1598, 1498, 1284, 1258, 1232, 1064, 803, 749; HRMS (EI): Calculated for C$_{13}$H$_{20}$BrNSi [M]$^+$: 297.0548. Found: 297.0546.

[Example 17] Preparation of 8-bromo-3-(diethylsilyl)-2-methyl-1,2,3,4-tetrahydroquinoline (17b)

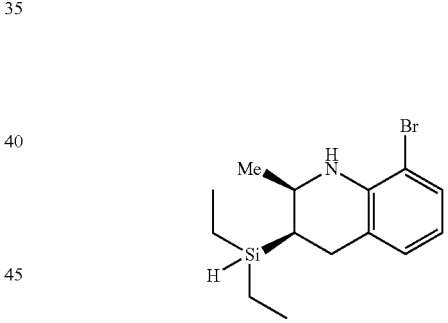

8-bromo-3-(diethylsilyl)-2-methyl-1,2,3,4-tetrahydroquinoline (17b) (yield: 81%) was obtained by the same method as Example 1 above except for using 8-bromo-2-methylquinoline (17a) instead of quinoline (1a) and stirring at 23° C. for 6 hours.

Colorless oil; $^1$H NMR (600 MHz, CDCl$_3$) δ 7.38-7.07 (m, 1H), 6.89 (dt, J=7.5, 1.5 Hz, 1H), 6.44 (td, J=7.7, 1.2 Hz, 1H), 4.54 (s, 1H), 3.77 (dt, J=6.8, 3.4 Hz, 1H), 3.69 (ddd, J=5.3, 2.3, 1.2 Hz, 1H), 3.03-2.43 (m, 2H), 1.47 (ddt, J=8.6, 5.0, 1.9 Hz, 1H), 1.23 (dd, J=6.6, 1.5 Hz, 3H), 1.00 (dtt, J=18.5, 7.8, 1.3 Hz, 6H), 0.78-0.30 (m, 4H); $^{13}$C NMR (150 MHz, CDCl$_3$) δ 140.9, 130.0, 127.8, 122.63, 116.5, 108.9, 48.2, 26.5, 22.3, 20.4, 8.4, 8.38, 1.9, 1.7; $^{29}$Si NMR (120 MHz, CDCl$_3$) δ -1.14; IR (cm$^{-1}$): 3423, 2951, 2872, 2094, 1600, 1459, 1284, 1260, 1232, 1009, 918, 752; HRMS (ESI): Calculated for C$_{14}$H$_{23}$BrNSi [M+H]$^+$: 314.0763. Found: 314.0737.

[Example 18] Preparation of 3-(diethylsilyl)-6-(p-tolyloxy)-1,2,3,4-tetrahydroquinoline (20b)

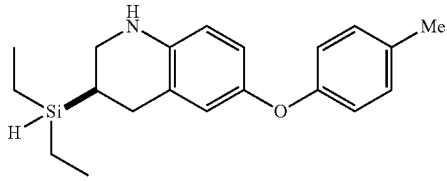 [SMILES: CC[SiH](CC)[C@H]1CNc2ccc(Oc3ccc(C)cc3)cc2C1]

3-(diethylsilyl)-6-(p-tolyloxy)-1,2,3,4-tetrahydroquinoline (20b) (yield: 88%) was obtained by the same method as Example 1 above except for using 6-(p-tolyloxy)quinoline (20a) instead of quinoline (1a) and stirring for 12 hours.

Bright yellow oil; $^1$H NMR (600 MHz, CDCl$_3$) δ 7.12-7.05 (m, 2H), 6.89-6.83 (m, 2H), 6.72-6.64 (m, 2H), 6.46 (d, J=8.5 Hz, 1H), 3.64 (q, J=3.1 Hz, 1H), 3.44-3.33 (m, 1H), 3.22 (t, J=11.4 Hz, 1H), 2.73 (d, J=8.5 Hz, 2H), 2.31 (s, 3H), 1.52-1.39 (m, 1H), 1.04 (t, J=7.9 Hz, 6H), 0.82-0.50 (m, 4H); $^{13}$C NMR (150 MHz, CDCl$_3$) δ 156.7, 147.8, 140.81, 131.2, 129.8 (2C), 123.1, 120.3, 118.4, 117.3 (2C), 115.2, 44.2, 29.2, 20.5, 17.7, 8.3 (2C), 1.3, 1.1; $^{29}$Si NMR (120 MHz, CDCl$_3$) δ 0.42; IR (cm$^{-1}$): 3406, 2951, 2872, 2093, 1607, 1495, 1286, 1226, 1011, 805; HRMS (EI): Calculated for C$_{20}$H$_{27}$NOSi [M]$^+$: 325.1862. Found: 325.1863.

[Example 19] Preparation of 3-(diethylsilyl)-4,6,8-trimethyl-1,2,3,4-tetrahydroquinoline (21b)

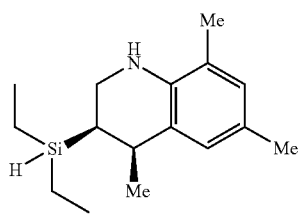 [SMILES: CC[SiH](CC)[C@H]1CNc2c(C)cc(C)cc2[C@H]1C]

3-(diethylsilyl)-4,6,8-trimethyl-1,2,3,4-tetrahydroquinoline (21b) (yield: 80%) was obtained by the same method as Example 1 above except for using 4,6,8-trimethylquinoline (21a) instead of quinoline (1a).

Colorless oil; $^1$H NMR (600 MHz, CDCl$_3$) δ 6.87-6.81 (m, 1H), 6.81-6.73 (m, 1H), 3.65 (q, J=3.1 Hz, 1H), 3.56 (dd, J=11.3, 3.6 Hz, 1H), 3.31 (dd, J=11.3, 6.3 Hz, 1H), 3.02-2.88 (m, 1H), 2.27 (s, 3H), 2.11 (s, 3H), 1.41 (d, J=6.9 Hz, 3H), 1.24 (dtd, J=5.1, 2.5, 1.2 Hz, 1H), 1.03 (td, J=7.9, 3.0 Hz, 6H), 0.65 (dddt, J=12.6, 8.1, 6.5, 3.0 Hz, 4H); $^{13}$C NMR (150 MHz, CDCl$_3$) δ 140.3, 128.5, 127.3, 126.5, 125.6, 121.4, 41.1, 32.3, 25.6, 25.2, 20.5, 17.2, 8.6, 8.5, 2.0, 1.9; $^{29}$Si NMR (120 MHz, CDCl$_3$) δ 0.63; IR (cm$^{-1}$) 2952, 2094, 1495, 1326, 1265, 1248, 1234, 1008, 856, 806; HRMS (EI): Calculated for C$_{16}$H$_{27}$NSi [M]$^+$: 261.1913. Found: 261.1913.

[Example 20] Preparation of 6-bromo-3-(diethylsilyl)-3-methyl-1,2,3,4-tetrahydroquinoline (22b)

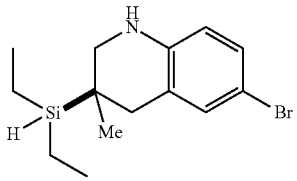 [SMILES: CC[SiH](CC)[C@@]1(C)CNc2ccc(Br)cc2C1]

6-bromo-3-(diethylsilyl)-3-methyl-1,2,3,4-tetrahydroquinoline (22b) (yield: 76%) was obtained by the same method as Example 1 above except for using 6-bromo-3-methylquinoline (22a) instead of quinoline (1a) and stirring for 12 hours.

Colorless oil; $^1$H NMR (600 MHz, CDCl$_3$) δ 7.02 (d, J=2.6 Hz, 2H), 6.32 (d, J=9.1 Hz, 1H), 3.82 (br, 1H), 3.47 (dd, J=4.6, 2.4 Hz, 1H), 3.26 (dd, J=11.4, 1.1 Hz, 1H), 2.94 (dd, J=11.6, 1.6 Hz, 1H), 2.81 (d, J=16.3 Hz, 1H), 2.39 (d, J=16.3 Hz, 1H), 1.14-0.82 (m, 9H), 0.63 (ddd, J=8.2, 6.5, 4.0 Hz, 4H); $^{13}$C NMR (150 MHz, CDCl$_3$) δ 143.01, 132.1, 129.2, 122.0, 115.1, 108.1, 49.7, 36.7, 20.7, 18.9, 8.9, 8.8, 0.8, 0.5; $^{29}$Si NMR (120 MHz, CDCl$_3$) δ 6.59; IR (cm$^{-1}$) 3429, 2953, 2915, 2874, 2098, 1640, 1493, 1460, 1376, 1302, 1276, 1236, 1084, 969, 802; HRMS (ESI): Calculated for C$_{14}$H$_{23}$BrNSi [M+H]$^+$: 314.0763. Found: 314.0750.

[Example 21] Preparation of 6-bromo-3-(diethylsilyl)-8-fluoro-1,2,3,4-tetrahydroquinoline (23b)

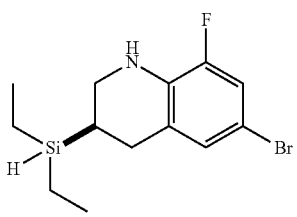 [SMILES: CC[SiH](CC)[C@H]1CNc2c(F)cc(Br)cc2C1]

6-bromo-3-(diethylsilyl)-8-fluoro-1,2,3,4-tetrahydroquinoline (23b) (yield: 90%) was obtained by the same method as Example 1 above except for using 6-bromo-8-fluoroquinoline (23a) instead of quinoline (1a) and stirring for 12 hours.

Colorless oil; $^1$H NMR (600 MHz, CDCl$_3$) δ 6.94 (dd, J=10.5, 2.1 Hz, 1H), 6.86 (dd, J=2.4, 1.2 Hz, 1H), 4.08 (s, br, 1H), 3.63 (q, J=3.1 Hz, 1H), 3.45 (ddd, J=11.6, 3.6, 1.8 Hz, 1H), 3.20 (t, J=11.5 Hz, 1H), 2.76 (ddd, J=16.6, 4.8, 1.8 Hz, 1H), 2.68 (dd, J=16.4, 11.8 Hz, 1H), 1.48-1.33 (m, 1H), 1.03 (ddd, J=8.6, 7.6, 1.2 Hz, 6H), 0.74-0.58 (m, 4H); $^{13}$C NMR (150 MHz, CDCl$_3$) δ 150.5 (d, J=242.1 Hz), 132.2 (d, J=11.9 Hz), 126.8 (d, J=3.0 Hz), 125.3 (d, J=4.4 Hz), 115.6 (d, J=21.6 Hz), 105.9, 43.2, 28.7 (d, J=3.0 Hz), 17.1, 8.3 (2C), 1.3, 1.2; $^{29}$Si NMR (120 MHz, CDCl$_3$) δ 0.28; $^{19}$F NMR (564 MHz, CDCl$_3$) δ −136.8 (d, J=10.5 Hz); IR (cm$^{-1}$) 2952, 2873, 2831, 2096, 1499, 1306, 1279, 1232, 1207, 991, 842, 806; HRMS (EI): Calculated for C$_{13}$H$_{19}$BrFNSi [M]$^+$: 315.0454. Found: 315.0451.

[Example 22] Preparation of 6-chloro-3-(diethylsilyl)-8-fluoro-1,2,3,4-tetrahydroquinoline (24b)

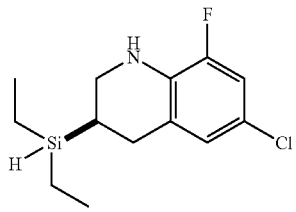

6-chloro-3-(diethylsilyl)-8-fluoro-1,2,3,4-tetrahydroquinoline (24b) (yield: 89%) was obtained by the same method as Example 1 above except for using 6-chloro-8-fluoroquinoline (24a) instead of quinoline (1a) and stirring at 23° C. for 10 mins.

Colorless oil; $^1$H NMR (600 MHz, CDCl$_3$) δ 6.81 (dd, J=10.8, 2.3 Hz, 1H), 6.73 (dd, J=2.5, 1.3 Hz, 1H), 4.04 (s, 1H), 3.64 (q, J=3.1 Hz, 1H), 3.45 (ddd, J=11.6, 3.5, 1.8 Hz, 1H), 3.21 (t, J=11.5 Hz, 1H), 2.76 (ddd, J=16.5, 4.8, 1.8 Hz, 1H), 2.68 (dd, J=16.4, 11.8 Hz, 1H), 1.50-1.31 (m, 1H), 1.04 (td, J=7.9, 1.4 Hz, 6H), 0.69 (dddd, J=10.8, 7.9, 4.8, 2.6 Hz, 4H); $^{13}$C NMR (150 MHz, CDCl$_3$) δ 150.3 (d, J=241.0 Hz), 131.7 (d, J=12.1 Hz), 124.7 (d, J=4.7 Hz), 123.9 (d, J=2.9 Hz), 119.4 (d, J=10.4 Hz), 112.9 (d, J=21.9 Hz), 43.2, 28.7 (d, J=3.1 Hz), 17.1, 8.3 (2C), 1.3, 1.1; $^{29}$Si NMR (120 MHz, CDCl$_3$) δ 0.34; $^{19}$F NMR (564 MHz, CDCl$_3$) δ -136.9 (d, J=10.8 Hz); IR (cm$^{-1}$) 2952, 2874, 2095, 1500, 1415, 1308, 1281, 1236, 992, 888, 843, 710; HRMS (EI): Calculated for C$_{13}$H$_{19}$ClFNSi [M]$^+$: 271.0959. Found: 271.0959.

[Example 23] Preparation of 6-bromo-3-(diethylsilyl)-5,7-difluoro-1,2,3,4-tetrahydroquinoline (25b)

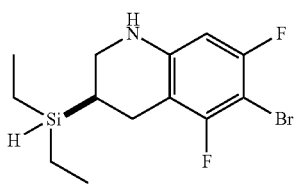 [SMILES: CC[SiH](CC)[C@H]1CNc2cc(F)c(Br)c(F)c2C1]

6-bromo-3-(diethylsilyl)-5,7-difluoro-1,2,3,4-tetrahydroquinoline (25b) (yield: 85%) was obtained by the same method as Example 1 above except for using 7-bromo-6,8-difluoroquinoline (25a) instead of quinoline (1a).

Colorless oil; $^1$H NMR (600 MHz, CDCl$_3$) δ 6.06 (dd, J=9.5, 1.1 Hz, 1H), 4.16 (s, br, 1H), 3.62 (q, J=3.1 Hz, 1H), 3.36 (ddd, J=11.7, 3.5, 1.9 Hz, 1H), 3.16 (t, J=11.5 Hz, 1H), 2.86 (ddt, J=16.5, 2.9, 1.4 Hz, 1H), 2.55-2.41 (m, 1H), 1.30 (ddd, J=11.4, 7.6, 4.1 Hz, 1H), 1.02 (td, J=7.9, 1.3 Hz, 6H), 0.85-0.57 (m, 4H); 13C NMR (150 MHz, CDCl$_3$) δ 158.6 (dd, J=130.4, 6.9 Hz), 157.0 (dd, J=130.1, 7.1 Hz), 145.2 (dd, J=12.6, 10.5 Hz), 105.7 (dd, J=22.5, 2.9 Hz), 96.8 (dd, J=25.8, 2.3 Hz), 82.5 (t, J=25.3 Hz), 43.4, 21.8 (d, J=3.0 Hz), 16.2, 8.3 (2C), 1.3, 1.1; $^{29}$Si NMR (120 MHz, CDCl$_3$) δ 0.38; $^{19}$F NMR (564 MHz, CDCl$_3$) δ -111.4, -111.5; IR (cm$^{-1}$) 2953, 2874, 2098, 1621, 1588, 1492, 1459, 1412, 1347, 1301, 1279, 1262, 1233, 1197, 1080, 1016, 806; HRMS (EI): Calculated for C$_{13}$H$_{18}$BrF$_2$NSi [M]$^+$: 333.0360. Found: 333.0361.

[Example 24] Preparation of 3-(diethylsilyl)-1,2,3,4-tetrahydrobenzo[h]quinoline (26b)

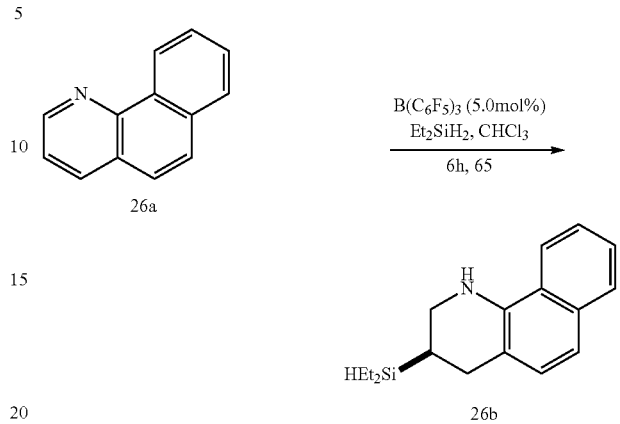

B(C$_6$F$_5$)$_3$ (0.025 mmol, 5.0 mol %) was dissolved in chloroform (0.50 mL) in a 2.5 mL reaction vial, then diethylsilane (2.0 mmol, 4.0 eq) and benzo[h]quinoline (26a, 0.50 mmol, 1.0 eq) were sequentially added thereto. The reaction mixture was stirred at 65° C. for 6 hours, cooled to room temperature, and filtrated by passing through a silica gel pad with dichloromethane (15 mL). After decompression concentration of the filtrate, the residue was purified by silica gel column chromatography (EA/Hx=5/95) to obtain 3-(diethylsilyl)-1,2,3,4-tetrahydrobenzo[h]quinoline (26b) (yield: 94%).

Colorless oil; $^1$H NMR (600 MHz, CDCl$_3$) δ 7.78-7.73 (m, 1H), 7.70 (dd, J=8.1, 1.7 Hz, 1H), 7.44-7.38 (m, 2H), 7.19 (d, J=8.2 Hz, 1H), 7.13 (d, J=8.3 Hz, 1H), 4.44 (br, 1H), 3.71 (d, J=3.1 Hz, 1H), 3.66-3.58 (m, 1H), 3.37 (t, J=11.6 Hz, 1H), 3.01-2.85 (m, 2H), 1.64-1.43 (m, 1H), 1.08 (t, J=7.9 Hz, 6H), 0.83-0.65 (m, 4H); $^{13}$C NMR (150 MHz, CDCl$_3$) δ 138.8, 133.0, 128.5, 128.2, 124.8, 124.6, 123.3, 119.3, 116.8, 116.2, 44.5, 29.6, 17.6, 8.4 (2C), 1.4, 1.2; $^{29}$Si NMR (120 MHz, CDCl$_3$) δ 0.34; IR (cm$^{-1}$): 3419, 3050, 2871, 2090, 1574, 1518, 1398, 1266, 1233, 1009, 789; HRMS (EI): Calculated for C$_{17}$H$_{23}$NSi [M]$^+$: 269.1600. Found: 269.1600.

[Example 25] Preparation of 2-(diethylsilyl)-1,2,3,4-tetrahydrobenzo[f]quinoline (27b)

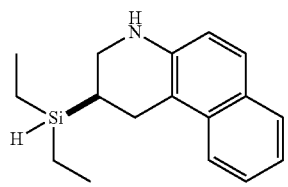 [SMILES: CC[SiH](CC)[C@H]1CNc2ccc3ccccc3c2C1]

2-(diethylsilyl)-1,2,3,4-tetrahydrobenzo[f]quinoline (27b) (yield: 85%) was obtained by the same method as Example 24 above except for using benzo[f]quinoline (27a) instead of benzo[h]quinoline (26a).

Colorless oil; $^1$H NMR (600 MHz, CDCl$_3$) δ 7.87 (d, J=8.3 Hz, 1H), 7.78 (d, J=8.0 Hz, 1H), 7.60 (d, J=8.6 Hz, 1H), 7.54 (td, J=6.6, 3.3 Hz, 1H), 7.33 (dd, J=8.0, 6.6 Hz, 1H), 6.80 (d, J=8.7 Hz, 1H), 4.08-3.76 (br, 1H), 3.84 (d, J=3.1 Hz, 1H), 3.45 (ddd, J=11.4, 3.4, 1.8 Hz, 1H), 3.30 (t, J=11.4 Hz, 2H), 2.98 (dd, J=16.3, 11.7 Hz, 1H), 1.66 (dt, J=5.6, 3.1 Hz, 1H), 1.18 (dd, J=7.9, 3.8 Hz, 6H), 0.89-0.77 (m, 4H); $^{13}$C NMR (150 MHz, CDCl$_3$) δ 141.8, 133.2, 128.3, 127.6, 126.9, 126.1, 121.4, 120.9, 118.3, 111.8, 43.5, 24.7, 17.4, 8.4 (2C), 1.4, 1.2; $^{29}$Si NMR (120 MHz, CDCl$_3$) δ 0.83; IR (cm-1): 3399, 2951, 2872, 2092, 1621, 1518, 1259, 1242, 1013, 805, 741; HRMS (EI): Calculated for C$_{17}$H$_{23}$NSi [M]$^+$: 269.1600. Found: 269.1602.

[Example 26] Preparation of 6-bromo-3-(diethylsilyl)-4-methyl-1,2,3,4-tetrahydroquinoline (44b)

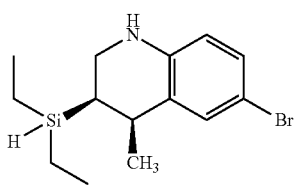 [SMILES: CC[SiH](CC)[C@H]1CNc2ccc(Br)cc2[C@H]1C]

6-bromo-3-(diethylsilyl)-4-methyl-1,2,3,4-tetrahydroquinoline (44b) (yield: 82%) was obtained by the same method as Example 1 above except for using 6-bromo-4-methylquinoline (44a) instead of quinoline (1a).

Colorless oil; $^1$H NMR (600 MHz, CDCl$_3$) δ 7.23-7.12 (m, 1H), 7.03 (d, J=8.5 Hz, 1H), 6.34 (d, J=8.5 Hz, 1H), 3.63-3.54 (m, 1H), 3.52-3.39 (m, 1H), 3.26-3.16 (m, 1H), 2.97-2.77 (m, 1H), 1.33 (dd, J=6.8, 1.5 Hz, 3H), 1.17 (d, J=2.0 Hz, 1H), 1.03-0.94 (m, 6H), 0.61 (dt, J=7.9, 3.9 Hz, 4H); $^{13}$C NMR (150 MHz, CDCl$_3$) δ 143.6, 131.4, 129.3, 128.8, 115.9, 108.6, 40.3, 32.2, 25.0, 24.7, 8.52, 8.46, 1.9, 1.8; $^{29}$Si NMR (120 MHz, CDCl$_3$) δ 0.06; IR (cm$^{-1}$) 2954, 2872, 2100, 1494, 1465, 1301, 1275, 1260, 1233, 1166, 805; HRMS (EI): Calculated for C$_{14}$H$_{22}$BrNSi [M]$^+$: 311.0705. Found: 311.0703.

Example II: Preparation of Silylative-Reduced Tetrahydrobenzoquinoline Compound (Chemical Formula 1-5)

[Example 27] Preparation of 2-(diethylsilyl)-1,2,3,4-tetrahydrobenzo[f]quinoline (32b)

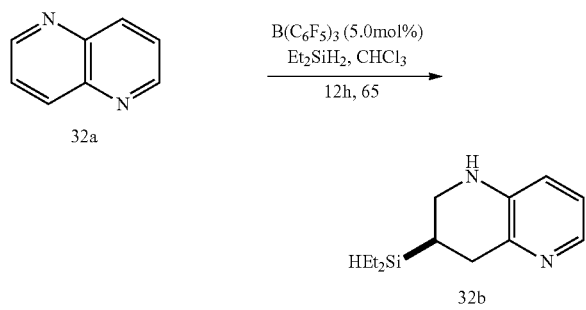

B(C$_6$F$_5$)$_3$ (0.025 mmol, 5.0 mol %) was dissolved in chloroform (0.50 mL) in a 2.5 mL reaction vial, then diethylsilane (4.0 mmol, 8.0 eq) and 1,5-naphthyridine (32a, 0.50 mmol, 1.0 eq) were sequentially added thereto. The reaction mixture was stirred at 65° C. for 24 hours, cooled to room temperature, and filtrated by passing through a silica gel pad with dichloromethane (15 mL). After decompression concentration of the filtrate, the residue was purified by silica gel column chromatography (EA/Hx=5/95) to obtain 2-(diethylsilyl)-1,2,3,4-tetrahydrobenzo[f]quinoline (32b) (yield: 34%).

Colorless oil; $^1$H NMR (600 MHz, CDCl$_3$) δ 7.81 (dd, J=4.6, 1.7 Hz, 1H), 6.85 (dd, J=8.1, 4.6 Hz, 1H), 6.68 (dd, J=7.7, 1.7 Hz, 1H), 3.95 (br, 1H), 3.62 (d, J=3.1 Hz, 1H), 3.40-3.27 (m, 1H), 3.19 (t, J=11.5 Hz, 1H), 2.95 (ddd, J=17.1, 4.8, 2.1 Hz, 1H), 2.81 (dd, J=16.9, 12.2 Hz, 1H), 1.53-1.43 (m, 1H), 1.00 (t, J=8.0 Hz, 6H), 0.74-0.57 (m, 4H); $^{13}$C NMR (150 MHz, CDCl$_3$) δ 142.9, 140.6, 137.7, 121.8, 120.2, 43.6, 32.3, 17.3, 8.3, 8.2, 1.3, 1.0; $^{29}$Si NMR (80 MHz, CDCl$_3$) δ 0.21; IR (cm$^{-1}$): 3314, 2953, 2874, 2099, 1583, 1556, 1451, 1368, 1259, 1233, 1006, 845, 727; HRMS (EI): Calculated for C$_{12}$H$_{20}$N$_2$Si [M]$^+$: 220.1396. Found: 220.1394.

Example III: Preparation of Silylative-Reduced Octahydro-Benzo-Phenanthroline Compound (Chemical Formula 1-6)

[Example 28] Preparation of 3,9-bis(diethylsilyl)-1,2,3,4,7,8,9,10-octahydro-1,7-phenanthroline (33b)

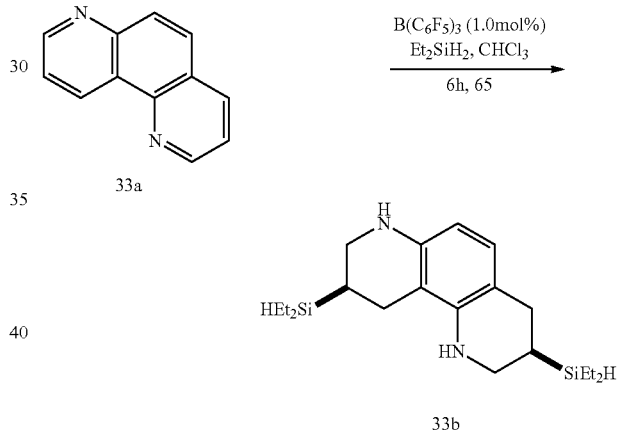

B(C$_6$F$_5$)$_3$ (0.005 mmol, 1.0 mol %) was dissolved in chloroform (0.50 mL) in a 2.5 mL reaction vial, then diethylsilane (4.0 mmol, 8.0 eq) and 1,7-phenanthroline (33a, 0.50 mmol, 1.0 eq) were sequentially added thereto. The reaction mixture was stirred at 65° C. for 6 hours, cooled to room temperature, and filtrated by passing through a silica gel pad with dichloromethane (15 mL). After decompression concentration of the filtrate, the residue was purified by silica gel column chromatography (EA/Hx=5/95) to obtain 3,9-bis(diethylsilyl)-1,2,3,4,7,8,9,10-octahydro-1,7-phenanthroline (33b) (yield: 72%).

Red oil; $^1$H NMR (600 MHz, CDCl$_3$) δ 6.68 (d, J=8.0 Hz, 1H), 5.97 (d, J=8.0 Hz, 1H), 3.69 (dd, J=16.1, 3.1 Hz, 2H), 3.63 (br, 2H), 3.51 (ddd, J=11.8, 3.4, 1.7 Hz, 1H), 3.32 (ddd, J=11.0, 3.1, 1.5 Hz, 1H), 3.27 (t, J=11.6 Hz, 1H), 3.15 (t, J=11.3 Hz, 1H), 2.80-2.68 (m, 2H), 2.48 (ddd, J=16.0, 5.9, 1.6 Hz, 1H), 2.34 (dd, J=15.9, 11.5 Hz, 1H), 1.56 (dddd, J=11.4, 8.5, 5.8, 2.9 Hz, 1H), 1.46 (dtd, J=11.2, 5.7, 3.0 Hz, 1H), 1.16-1.01 (m, 12H), 0.73 (ddd, J=9.1, 4.7, 1.8 Hz, 8H); $^{13}$C NMR (150 MHz, CDCl$_3$) δ 143.5, 141.9, 126.8, 111.2, 106.0, 104.4, 44.4, 43.3, 29.0, 23.3, 18.1, 17.9, 8.36, 8.33, 8.31 (2C), 1.4, 1.3, 1.19, 1.16; $^{29}$Si NMR (120 MHz, CDCl$_3$)

δ 0.70, 0.33; IR (cm-1) 2952, 2873, 2825, 2093, 1609, 1488, 1336, 1240, 1123, 1012, 808; HRMS (EI): Calculated for $C_{20}H_{36}N_2Si_2$ $[M]^+$: 360.2417. Found: 360.2415.

Example IV: Preparation of Silylative-Reduced Tetrahydroquinoline Compound (Chemical Formula 5-1)

[Example 29] Preparation of 8-{6-bromo-3-(diethylsilyl)-3,4-dihydroquinolin-1(2H)-ylsulfonyl}quinoline (13b-QUS)

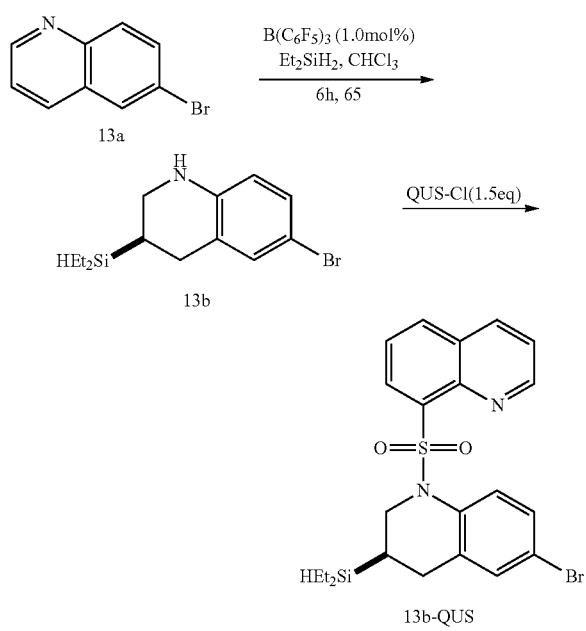

$B(C_6F_5)_3$ (0.0050 mmol, 1.0 mol %) was dissolved in chloroform (0.50 mL) in a 2.5 mL reaction vial, then diethylsilane (2.0 mmol, 4.0 eq) and 6-bromoquinoline (13a, 0.50 mmol, 1.0 eq) were sequentially added thereto. The reaction mixture was stirred at 65° C. for 6 hours, cooled to room temperature, and filtrated by passing through a silica gel pad with dichloromethane (15 mL) and methanol (2 mL). After decompression concentration of the filtrate, dichloromethane (2 mL) was added to the residue, and in the presence of triethylamine (1.5 mmol, 3.0 eq), QUS-Cl (8-quinolinesulfonyl chloride, 0.75 mmol, 1.5 eq) was added thereto at 0° C. to room temperature. The reaction mixture was stirred at room temperature for 12 hours, followed by decompression concentration, and the obtained residue was purified by silica gel column chromatography (EA/Hx=3/7) to obtain 8-{6-bromo-3-(diethylsilyl)-3,4-dihydroquinolin-1(2H)-ylsulfonyl}quinoline (13b-QUS) (yield: 82%).

Colorless solid; m.p. 118-120° C.; $^1$H NMR (600 MHz, $CDCl_3$) δ 8.85 (dd, J=4.1, 1.9 Hz, 1H), 8.55 (dt, J=7.3, 1.4 Hz, 1H), 8.15 (dt, J=8.4, 1.8 Hz, 1H), 7.98 (dt, J=8.2, 1.5 Hz, 1H), 7.66-7.54 (m, 1H), 7.50 (d, J=8.9 Hz, 1H), 7.43 (dd, J=8.2, 4.2 Hz, 1H), 7.07 (dd, J=8.9, 2.3 Hz, 1H), 7.01 (d, J=2.5 Hz, 1H), 4.63 (ddd, J=12.6, 4.1, 1.7 Hz, 1H), 3.96 (t, J=12.8 Hz, 1H), 3.68 (q, J=3.1 Hz, 1H), 2.77-2.39 (m, 2H), 1.34 (dd, J=2.6, 1.4 Hz, 1H), 1.00 (q, J=8.1 Hz, 6H), 0.78-0.59 (m, 4H); $^{13}$C NMR (150 MHz, $CDCl_3$) δ 150.8, 143.7, 137.1, 136.3, 133.8, 133.5, 133.4, 131.6, 130.8, 129.0, 128.8, 125.2, 122.5, 122.0, 115.4, 49.5, 29.7, 18.9, 8.2, 8.19, 1.1, 1.0; $^{29}$Si NMR (120 MHz, $CDCl_3$) δ −0.20; IR (cm$^{-1}$): 2953, 2135, 1478, 1338, 1208, 1166, 1143, 1026, 808, 781, 565; HRMS (EI): Calculated for $C_{22}H_{25}BrN_2O_2SSi$ $[M]^+$: 488.0589. Found: 488.0592.

[Example 30] Preparation of 8-{6-bromo-3-(diethylsilyl)-2-methyl-3,4-dihydroquinolin-1(2H)-ylsulfonyl}quinoline (18b-QUS)

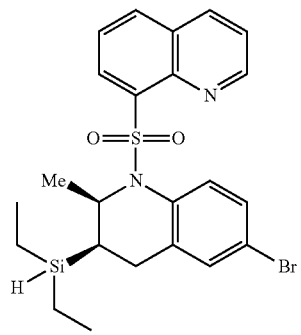 [SMILES: CC[SiH](CC)[C@@H]1Cc2cc(Br)ccc2N(S(=O)(=O)c2cccc3cccnc23)[C@@H]1C]

8-{6-bromo-3-(diethylsilyl)-2-methyl-3,4-dihydroquinolin-1(2H)-ylsulfonyl}quinoline (18b-QUS) (yield: 49%) was obtained by the same method as Example 29 above except for using 6-bromo-2-methylquinoline (18a) instead of 6-bromoquinoline (13a).

Colorless solid; m.p. 152-154° C.; $^1$H NMR (400 MHz, $CDCl_3$) δ 8.72 (dd, J=4.1, 1.7 Hz, 1H), 8.55 (dd, J=7.5, 1.3 Hz, 1H), 8.15 (dd, J=8.3, 1.6 Hz, 1H), 8.00 (dd, J=8.2, 1.4 Hz, 1H), 7.69-7.55 (m, 2H), 7.46-7.36 (m, 1H), 7.19 (dd, J=9.0, 2.4 Hz, 1H), 7.13 (dd, J=2.5, 1.2 Hz, 1H), 4.99 (dd, J=6.9, 3.4 Hz, 1H), 3.56 (dq, J=3.6, 1.9 Hz, 1H), 2.71 (dd, J=17.5, 14.0 Hz, 1H), 2.48 (dd, J=17.6, 5.8 Hz, 1H), 1.19 (d, J=6.9 Hz, 4H), 0.93 (t, J=7.9 Hz, 3H), 0.81 (t, J=7.9 Hz, 3H), 0.68-0.49 (m, 4H); $^{13}$C NMR (100 MHz, $CDCl_3$) δ 150.8, 143.8, 137.1, 136.2, 135.1, 133.7, 132.9, 131.23, 129.3, 128.9, 128.8, 125.2, 125.1, 121.9, 115.9, 52.4, 24.9, 20.9, 16.7, 8.0, 7.8, 1.2, 0.9; $^{29}$Si NMR (120 MHz, $CDCl_3$) δ −0.72; IR (cm$^{-1}$): 2954, 2872, 2085, 1477, 1332, 1228, 1162, 1144, 1005, 815, 784, 580; HRMS (ESI): Calculated for $C_{23}H_{27}BrNaN_2O_2SSi$ $[M+Na]^+$: 525.0644. Found: 525.0653.

Example V: Preparation of Silylative-Reduced Tetrahydroquinoline Compound (Chemical Formula 5-2)

[Example 31] Preparation of 8-{4-diethylsilyl)-3,4-dihydroisoquinolin-2(1H)-ylsulfonyl}quinoline (28b)

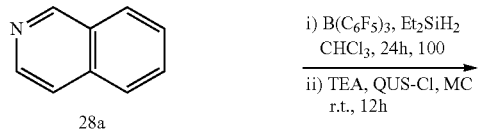

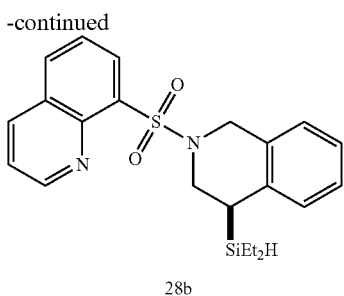

28b

B(C$_6$F$_5$)$_3$ (0.005 mmol, 1.0 mol %) was dissolved in chloroform (0.50 mL) in a 2.5 mL reaction vial, then diethylsilane (4.0 mmol, 8.0 eq) and isoquinoline (28a, 0.50 mmol, 1.0 eq) were sequentially added thereto. The reaction mixture was stirred at 100° C. for 24 hours, cooled to room temperature, and filtrated by passing through a silica gel pad with dichloromethane (15 mL). After decompression concentration of the filtrate, dichloromethane (2 mL) was added to the residue, and in the presence of triethylamine (1.5 mmol, 3.0 eq), QUS-Cl (8-quinolinesulfonyl chloride, 0.75 mmol, 1.5 eq) was added thereto at 0° C. The reaction mixture was stirred at room temperature for 12 hours, followed by decompression concentration, and the obtained residue was purified by silica gel column chromatography (EA/Hx=3/7) to obtain 8-{4-diethylsilyl)-3,4-dihydroisoquinolin-2(1H)-ylsulfonyl}quinoline (28b) (yield: 44%).

White solid; m.p. 85-87° C.; $^1$H NMR (400 MHz, CDCl$_3$) δ 9.04 (dd, J=4.2, 1.8 Hz, 1H), 8.58 (dd, J=7.4, 1.4 Hz, 1H), 8.23 (dd, J=8.4, 1.9 Hz, 1H), 8.05 (dd, J=8.1, 1.4 Hz, 1H), 7.66 (t, J=7.8 Hz, 1H), 7.49 (dd, J=8.3, 4.2 Hz, 1H), 7.18-6.86 (m, 4H), 4.78 (d, J=15.4 Hz, 1H), 4.40 (d, J=15.4 Hz, 1H), 4.29 (dd, J=12.5, 3.1 Hz, 1H), 3.83 (d, J=3.1 Hz, 1H), 3.51 (dd, J=12.5, 4.1 Hz, 1H), 2.61 (d, J=3.2 Hz, 1H), 0.98 (t, J=7.8 Hz, 3H), 0.91 (t, J=7.8 Hz, 3H), 0.77 (td, J=7.5, 4.0 Hz, 4H); $^{13}$C NMR (100 MHz, CDCl$_3$) δ 151.1, 144.2, 136.7, 136.3, 136.3, 133.5, 133.4, 131.2, 128.8, 127.7, 126.3, 126.2, 125.4, 124.8, 121.9, 47.3, 46.3, 27.9, 8.3, 8.1, 1.89, 1.82; $^{29}$Si NMR (120 MHz, CDCl$_3$): δ 2.61; IR (cm$^{-1}$): 2951, 2872, 2097, 1610, 1560, 1371, 1330, 1284, 1237, 1211, 1162, 1143, 1052, 868, 790; HRMS (FAB): Calculated for C$_{22}$H$_{27}$N$_2$O$_2$SSi [M+H]$^+$: 411.1563. Found: 411.1560.

[Example 32] Preparation of 8-{8-Bromo-4-(diethylsilyl)-3,4-dihydroisoquinolin-2(1H)-ylsulfonyl}quinoline (29b)

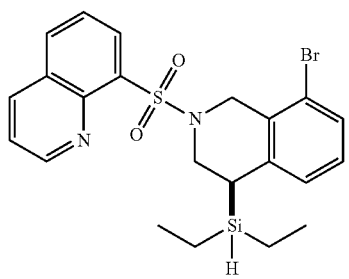 [SMILES: CC[SiH](CC)[C@H]1CN(S(=O)(=O)c2cccc3cccnc23)Cc2c(Br)cccc21]

8-{8-bromo-4-(diethylsilyl)-3,4-dihydroisoquinolin-2(1H)-ylsulfonyl}quinoline (29b) (yield: 66%) was obtained by the same method as Example 31 above except for using 8-bromoisoquinoline (29a) instead of isoquinoline (28a).

White solid; m.p. 99-101° C.; $^1$H NMR (600 MHz, CDCl$_3$) δ 9.00 (dd, J=4.1, 2.0 Hz, 1H), 8.64-8.46 (m, 1H), 8.19 (dd, J=8.4, 1.9 Hz, 1H), 8.08-7.90 (m, 1H), 7.61 (td, J=7.9, 3.0 Hz, 1H), 7.50-7.37 (m, 1H), 7.24 (d, J=7.7 Hz, 1H), 7.02-6.77 (m, 2H), 4.73 (d, J=16.4 Hz, 1H), 4.41-4.20 (m, 2H), 3.80 (q, J=3.2 Hz, 1H), 3.42 (dd, J=12.6, 3.9 Hz, 1H), 2.56 (t, J=3.4 Hz, 1H), 0.94 (dd, J=8.8, 7.1 Hz, 3H), 0.87 (t, J=7.9 Hz, 3H), 0.80-0.60 (m, 4H); $^{13}$C NMR (150 MHz, CDCl$_3$) δ 151.0, 144.1, 139.7, 136.3 (2C), 133.53, 133.47, 130.5, 128.8, 128.9, 127.3, 126.9, 125.4, 122.5, 121.9, 48.5, 45.9, 28.4, 8.3, 8.1, 1.8, 1.7; $^{29}$Si NMR (120 MHz, CDCl$_3$) δ 3.12; IR (cm$^{-1}$): 2952, 2871, 2101, 1559, 1457, 1274, 1238, 1211, 1160, 953, 875, 787; HRMS (FAB): Calculated for C$_{22}$H$_{26}$BrN$_2$O$_2$SSi [M+H]$^+$: 489.0668. Found: 489.0666.

[Example 33] Preparation of 8-[{5-chloro-4-(diethylsilyl)-3,4-dihydroisoquinolin-2(1H)-yl}sulfonyl]quinoline (30b)

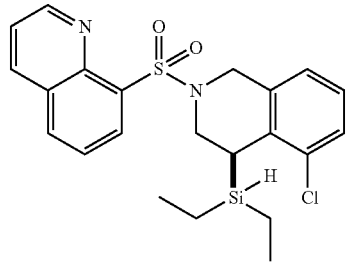 [SMILES: CC[SiH](CC)[C@H]1CN(S(=O)(=O)c2cccc3cccnc23)Cc2cccc(Cl)c21]

8-[{5-chloro-4-(diethylsilyl)-3,4-dihydroisoquinolin-2(1H)-yl}sulfonyl]quinoline (30b) (yield: 81%) was obtained by the same method as Example 31 above except for using 5-chloroisoquinoline (30a) instead of isoquinoline (28a).

White solid; m.p. 129-131° C.; $^1$H NMR (600 MHz, CDCl$_3$) δ 9.02 (dd, J=4.2, 1.8 Hz, 1H), 8.56 (dd, J=7.4, 1.4 Hz, 1H), 8.21 (dd, J=8.3, 1.8 Hz, 1H), 8.03 (dd, J=8.2, 1.4 Hz, 1H), 7.65 (dd, J=8.2, 7.4 Hz, 1H), 7.48 (dd, J=8.3, 4.2 Hz, 1H), 7.21-7.11 (m, 1H), 6.97 (t, J=7.8 Hz, 1H), 6.94-6.85 (m, 1H), 4.82 (d, J=15.6 Hz, 1H), 4.48-4.33 (m, 2H), 3.81 (d, J=3.3 Hz, 1H), 3.31 (dd, J=12.1, 3.5 Hz, 1H), 3.04-2.95 (m, 1H), 0.94 (t, J=7.8 Hz, 3H), 0.87 (t, J=7.9 Hz, 3H), 0.81 (ddd, J=7.9, 7.0, 4.0 Hz, 1H), 0.76-0.68 (m, 1H), 0.65 (ddt, J=14.9, 8.1, 3.7 Hz, 2H); $^{13}$C NMR (150 MHz, CDCl$_3$) δ 151.2, 144.3, 136.4, 136.3, 136.2, 133.9, 133.54, 133.52, 132.4, 129.0, 127.4, 125.6, 125.5, 125.0, 122.0, 47.0, 46.6, 26.5, 8.4, 8.2, 2.9, 2.3; $^{29}$Si NMR (120 MHz, CDCl$_3$) δ 1.30; IR (cm$^{-1}$) 2952, 2872, 2117, 1332, 1256, 1238, 1212, 1163, 833, 790, 586; HRMS (EI): Calculated for C$_{22}$H$_{25}$ClN$_2$O$_2$SSi [M]$^+$: 444.1095. Found: 444.1092.

[Example 34] Preparation of 8-[{5-Bromo-4-(diethylsilyl)-3,4-dihydroisoquinolin-2(1H)-yl}sulfonyl]quinoline (31b)

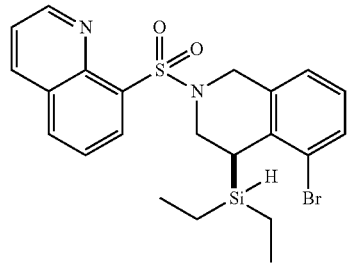 [SMILES: CC[SiH](CC)[C@H]1CN(S(=O)(=O)c2cccc3cccnc23)Cc2cccc(Br)c21]

8-[{5-bromo-4-(diethylsilyl)-3,4-dihydroisoquinolin-2(1H)-yl}sulfonyl]quinoline (31b) (yield: 71%) was obtained by the same method as Example 31 above except for using 5-bromoisoquinoline (31a) instead of isoquinoline (28a).

Semi-solid; $^1$H NMR (600 MHz, CDCl$_3$) δ 9.01 (dd, J=4.2, 1.8 Hz, 1H), 8.55 (dd, J=7.3, 1.5 Hz, 1H), 8.20 (dd, J=8.4, 1.8 Hz, 1H), 8.02 (dd, J=8.3, 1.5 Hz, 1H), 7.64 (t, J=7.8 Hz, 1H), 7.47 (dd, J=8.3, 4.2 Hz, 1H), 7.33 (dd, J=7.8, 1.3 Hz, 1H), 6.94 (dd, J=7.8, 1.4 Hz, 1H), 6.88 (t, J=7.8 Hz, 1H), 4.81 (d, J=15.6 Hz, 1H), 4.42 (d, J=15.6 Hz, 1H), 4.37 (dd, J=12.0, 2.0 Hz, 1H), 3.84 (d, J=3.3 Hz, 1H), 3.31 (dd, J=12.0, 3.5 Hz, 1H), 2.99 (d, J=2.7 Hz, 1H), 0.93 (t, J=7.8 Hz, 3H), 0.88 (t, J=7.9 Hz, 3H), 0.86-0.60 (m, 4H); $^{13}$C NMR (150 MHz, CDCl$_3$) δ 151.1, 144.2, 137.8, 136.4, 136.2, 133.8, 133.7, 133.5, 130.8, 128.9, 126.0, 125.7, 125.5, 123.4, 122.0, 47.0, 46.6, 29.1, 8.4, 8.2, 2.9, 2.3; $^{29}$Si NMR (120 MHz, CDCl$_3$) δ 1.07; IR (cm$^{-1}$) 2871, 2118, 1561, 1493, 1437, 1332, 1239, 1221, 1191, 1162, 1147, 1070, 1052, 832, 789, 586; HRMS (EI): Calculated for C$_{22}$H$_{25}$ClN$_2$O$_2$SSi [M]$^+$: 488.0589. Found: 488.0588.

Example VI: Preparation of Silylative-Reduced Piperidine Compound (Chemical Formula 5-3)

[Example 35] Preparation of 5-(diethylsilyl)-2-methyl-1-(4-nitrophenylsulfonyl)piperidine (34b)

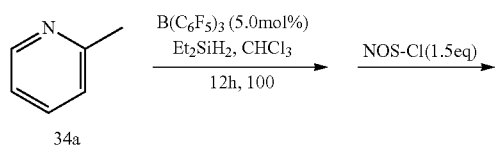

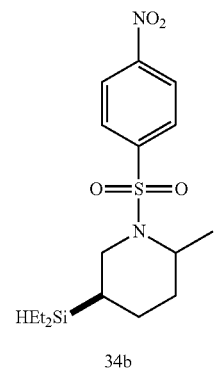

B(C$_6$F$_5$)$_3$ (0.025 mmol, 5.0 mol %) was dissolved in chloroform (0.50 mL) in a 2.5 mL reaction vial, then diethylsilane (4.0 mmol, 8.0 eq) and 2-methylpyridine (34a, 0.50 mmol, 1.0 eq) were sequentially added thereto. The reaction mixture was stirred at 100° C. for 12 hours, cooled to room temperature, and filtrated by passing through a silica gel pad with dichloromethane (15 mL). After decompression concentration of the filtrate, dichloromethane (2 mL) was added to the residue, and in the presence of triethylamine (1.5 mmol, 3.0 eq), NOS—Cl (4-nitrobenzenesulfonyl chloride, 0.75 mmol, 1.5 eq) was added thereto at 0° C. The reaction mixture was stirred at room temperature for 12 hours, followed by decompression concentration, and the obtained residue was purified by silica gel column chromatography (EA/Hx=3/7) to obtain 5-(diethylsilyl)-2-methyl-1-(4-nitrophenylsulfonyl)piperidine (34b) (yield: 72%).

Colorless solid; m.p. 51-53° C.; $^1$H NMR (600 MHz, CDCl$_3$) δ 8.32 (d, J=8.8 Hz, 2H), 7.97 (d, J=8.8 Hz, 2H), 3.91-3.68 (m, 1H), 3.67-3.47 (m, 2H), 3.27 (dd, J=12.6, 6.0 Hz, 1H), 1.82 (d, J=3.7 Hz, 2H), 1.55-1.36 (m, 2H), 1.22 (td, J=5.3, 4.4, 2.2 Hz, 1H), 1.11 (d, J=6.8 Hz, 3H), 0.95 (q, J=8.2 Hz, 6H), 0.70-0.53 (m, 4H); $^{13}$C NMR (150 MHz, CDCl$_3$) δ 149.7, 146.4, 128.3 (2C), 124.1 (2C), 51.4, 45.0, 31.0, 21.5, 20.6, 17.4, 8.2, 8.1, 1.3, 1.2; $^{29}$Si NMR (120 MHz, CDCl$_3$) δ −2.90; IR (cm$^{-1}$): 2950, 2873, 2099, 1529, 1348, 1234, 1209, 1166, 854, 803, 689; HRMS (ESI): Calculated for C$_{16}$H$_{27}$N$_2$O$_4$SSi [M+H]$^+$: 371.1461. Found: 371.1459.

Example VII: Preparation of Silylative-Reduced Tetrahydroquinoline Compound (Chemical Formula 5-4)

[Example 36] Preparation of (6-bromo-2-methyl-1,2,3,4-tetrahydroquinolin-3-yl)diethylsilanol (18b)

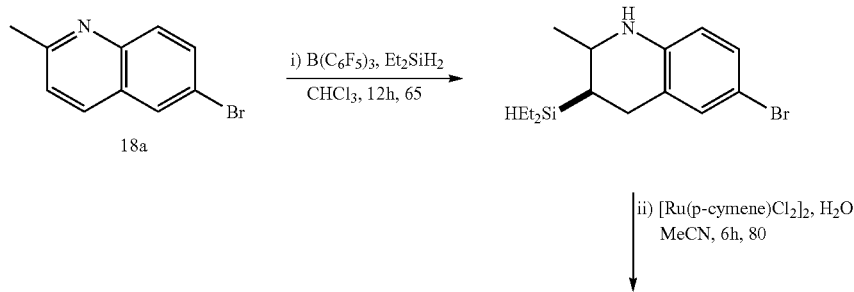

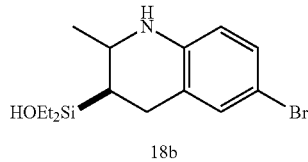

18b

B(C$_6$F$_5$)$_3$ (0.0050 mmol, 1.0 mol %) was dissolved in chloroform (0.50 mL) in a 2.5 mL reaction vial, then diethylsilane (4.0 mmol, 8.0 eq) and 6-bromo-2-methylquinoline (18a, 0.50 mmol, 1.0 eq) were sequentially added thereto. The reaction mixture was stirred at 65° C. for 12 hours, cooled to room temperature, and filtrated by passing through a silica gel pad with dichloromethane (15 mL) and methanol (2 mL). After decompression concentration of the filtrate, acetonitrile (3.0 mL) was added to the residue, and [Ru(p-cymene)Cl$_2$]$_2$ (0.025 mmol, 5.0 mol %) and deionized water (10 mmol, 20 eq) were added thereto. The reaction mixture was stirred at 80° C. for 6 hours, followed by decompression concentration, and the obtained residue was purified by silica gel column chromatography (EA/Hx=3/7) to obtain (6-bromo-2-methyl-1,2,3,4-tetrahydroquinolin-3-yl)diethylsilanol (18b) (yield: 58%).

Colorless oil; $^1$H NMR (600 MHz, CDCl$_3$) δ 6.85 (dt, J=8.1, 1.0 Hz, 1H), 6.56 (dd, J=8.1, 2.1 Hz, 1H), 6.44 (d, J=2.1 Hz, 1H), 3.68 (dd, J=6.6, 3.3 Hz, 1H), 2.77 (d, J=7.5 Hz, 2H), 1.38 (td, J=7.5, 3.3 Hz, 1H), 1.25 (d, J=6.6 Hz, 3H), 0.99 (t, J=8.0 Hz, 3H), 0.95 (t, J=8.0 Hz, 3H), 0.74-0.56 (m, 4H); $^{13}$C NMR (150 MHz, CDCl$_3$) δ 144.9, 131.9, 130.0, 119.8, 116.9, 114.1, 48.2, 25.2, 24.8, 20.8, 6.6, 6.5, 6.3, 5.7; $^{29}$Si NMR (120 MHz, CDCl$_3$) δ 17.04; IR (cm$^{-1}$): 3392, 3351, 2955, 2875, 1599, 1491, 1267, 1239, 1207, 1005, 821, 719; HRMS (EI): Calculated for C$_{14}$H$_{22}$BrNOSi [M]$^+$: 327.0654. Found: 327.0653.

[Example 37] Preparation of (2,8-dimethyl-1,2,3,4-tetrahydroquinolin-3-yl)diethylsilanol (19b)

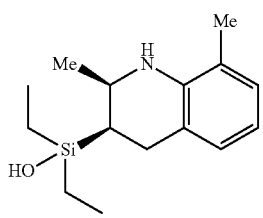 [SMILES: CC[Si](O)(CC)[C@@H]1Cc2cccc(C)c2N[C@@H]1C]

(2,8-dimethyl-1,2,3,4-tetrahydroquinolin-3-yl)diethylsilanol (19b) (yield: 55%) was obtained by the same method as Example 36 above except for using 2,8-dimethylquinoline (19a) instead of 6-bromo-2-methylquinoline (18a).

Colorless oil; $^1$H NMR (400 MHz, CDCl$_3$) δ 6.92 (td, J=6.0, 2.7 Hz, 2H), 6.63 (t, J=7.4 Hz, 1H), 3.82 (dd, J=6.7, 3.2 Hz, 1H), 2.92 (dd, J=12.1, 7.0 Hz, 2H), 2.11 (s, 3H), 1.52-1.42 (m, 1H), 1.40-1.33 (d, J=7.9 Hz, 3H), 1.10-1.01 (m, 3H), 0.97 (t, J=7.9 Hz, 3H), 0.80-0.55 (m, 4H); $^{13}$C NMR (100 MHz, CDCl$_3$) δ 141.9, 127.9, 127.0, 121.8, 121.2, 117.0, 49.2, 26.7, 24.8, 21.4, 17.2, 6.7, 6.6, 6.5, 5.7; $^{29}$Si NMR (120 MHz, CDCl$_3$) δ 17.78; IR (cm$^{-1}$): 3413, 2955, 2874, 1597, 1476, 1265, 1236, 1055, 754; HRMS (EI): Calculated for C$_{15}$H$_{25}$NOSi [M]$^+$: 263.1705. Found: 263.1704.

[Example 38] Preparation of (7-chloro-2-methyl-1,2,3,4-tetrahydroquinolin-3-yl)diethylsilanol (43b)

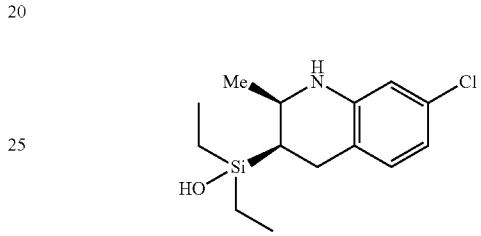

(7-chloro-2-methyl-1,2,3,4-tetrahydroquinolin-3-yl)diethylsilanol (43b) (yield: 67%) was obtained by the same method as Example 36 above except for using 7-chloro-2-methylquinoline (43a) instead of 6-bromo-2-methylquinoline (18a).

Colorless liquid; $^1$H NMR (600 MHz, CDCl$_3$) δ 7.07 (dd, J=2.2, 1.1 Hz, 1H), 7.03 (dd, J=8.5, 2.3 Hz, 1H), 6.34 (d, J=8.5 Hz, 1H), 3.67 (qd, J=6.6, 3.3 Hz, 1H), 2.79 (d, J=7.4 Hz, 2H), 1.36 (td, J=7.4, 3.2 Hz, 1H), 1.25 (d, J=6.6 Hz, 3H), 0.99 (t, J=8.0 Hz, 3H), 0.94 (t, J=7.9 Hz, 3H), 0.74-0.55 (m, 4H); $^{13}$C NMR (150 MHz, CDCl$_3$) δ 142.9, 131.5, 129.4, 123.6, 116.2, 108.8, 48.5, 25.7, 24.6, 20.8, 6.6, 6.5, 6.3, 5.7; $^{29}$Si NMR (120 MHz, CDCl$_3$) δ 17.06; IR (cm$^{-1}$): 3397, 2955, 2914, 2876, 1601, 1579, 1493, 1314, 1268, 1241, 1088, 969, 724; HRMS (ESI): Calculated for C$_{14}$H$_{23}$ClNOSi [M+H]$^+$: 284.1237. Found: 284.1220.

Example VIII: Preparation of Silylative-Reduced N-Heterocyclic Compound (Chemical Formula 5-5)

[Example 39] Preparation of 1,2,2,4,4-pentamethyl-7-(quinolin-8-ylsulfonyl)-3-oxa-7-aza-2,4-disilabicyclo[3.3.1]nonane (38b)

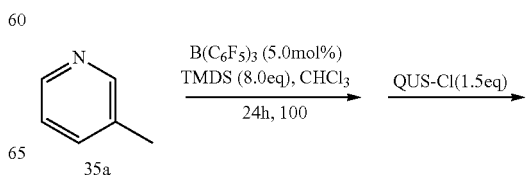

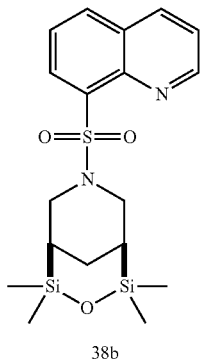

38b

B(C$_6$F$_5$)$_3$ (0.025 mmol, 5.0 mol %) was dissolved in chloroform (0.50 mL) in a 2.5 mL reaction vial, then 3-methyl pyridine (35a) was added thereto and stirred for 5 mins. Next, TMDS (tetramethyldisiloxane, 4.0 mmol, 8.0 eq) was added thereto and stirred at 100° C. for 24 hours. The reaction mixture was cooled to room temperature and filtrated by passing through a silica gel pad with dichloromethane (15 mL). After decompression concentration of the filtrate, triethylamine (1.5 mmol, 3.0 eq) and QUS-Cl (8-quinolinesulfonyl chloride, 0.75 mmol, 1.5 eq) were added thereto at 0° C. and stirred for 12 hours, then the residue obtained by decompression concentration was purified by silica gel column chromatography (EA/Hx=3/7) to obtain 1,2,2,4,4-pentamethyl-7-(quinolin-8-ylsulfonyl)-3-oxa-7-aza-2,4-disilabicyclo[3.3.1]nonane (38b) (yield: 43%) as a derivative having a silanol group introduced thereinto.

Colorless solid; m.p. 101-103° C.; $^1$H NMR (600 MHz, CDCl$_3$) δ 9.06 (dd, J=4.1, 1.8 Hz, 1H), 8.49 (dd, J=7.3, 1.2 Hz, 1H), 8.22 (dd, J=8.3, 1.8 Hz, 1H), 8.03 (dd, J=8.1, 1.4 Hz, 1H), 7.68-7.56 (m, 1H), 7.50 (dd, J=8.3, 4.2 Hz, 1H), 4.20 (dd, J=11.9, 1.8 Hz, 1H), 4.06 (d, J=11.8 Hz, 1H), 2.62 (dd, J=11.7, 3.5 Hz, 1H), 2.17-1.99 (m, 2H), 1.19 (d, J=4.8 Hz, 1H), 0.90 (dd, J=2.8, 1.3 Hz, 1H), 0.68 (s, 3H), 0.40 (s, 3H), 0.36 (s, 3H), 0.10 (s, 3H), 0.08 (s, 3H); $^{13}$C NMR (150 MHz, CDCl$_3$) δ 151.0, 144.5, 136.3, 135.7, 134.0, 133.4, 128.9, 125.4, 121.8, 57.6, 50.1, 36.1, 23.6, 23.4, 22.5, 0.0, −1.4, −1.6, −3.1; $^{29}$Si NMR (120 MHz, CDCl$_3$) δ 16.48, 13.47; IR (cm$^{-1}$): 2953, 1491, 1460, 1333, 1297, 1251, 1162, 996, 825, 785; HRMS (FAB): Calculated for C$_{19}$H$_{29}$N$_2$O$_3$SSi$_2$ [M+H]$^+$: 421.1435. Found: 421.1437.

[Example 40] Preparation of 1-butyl-2,2,4,4-tetramethyl-7-(quinolin-8-ylsulfonyl)-3-oxa-7-aza-2,4-disilabicyclo[3.3.1]nonane (39b)

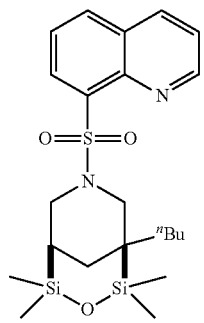

1-butyl-2,2,4,4-tetramethyl-7-(quinolin-8-ylsulfonyl)-3-oxa-7-aza-2,4-disilabicyclo[3.3.1]nonane (39b) was obtained by the same method as Example 39 above except for using 3-n-butyl pyridine (38a) instead of 3-methyl pyridine (35a).

Colorless oil; $^1$H NMR (600 MHz, CDCl$_3$): δ 9.06 (dd, J=4.2, 1.8 Hz, 1H), 8.49 (dd, J=7.4, 1.4 Hz, 1H), 8.23 (dd, J=8.4, 1.8 Hz, 1H), 8.03 (dd, J=8.2, 1.4 Hz, 1H), 7.63 (t, J=7.8 Hz, 1H), 7.50 (dd, J=8.3, 4.2 Hz, 1H), 4.34 (dt, J=12.0, 1.7 Hz, 1H), 4.24-4.07 (m, 1H), 2.56 (dd, J=11.6, 3.6 Hz, 1H), 2.09 (d, J=11.8 Hz, 1H), 2.04-1.96 (m, 1H), 1.37-1.13 (m, 5H), 1.13-1.05 (m, 1H), 0.86 (q, J=7.3, 6.4 Hz, 5H), 0.44 (s, 3H), 0.39 (s, 3H), 0.11 (s, 3H), 0.09 (s, 3H); $^{13}$C NMR (150 MHz, CDCl$_3$) δ 150.9, 144.6, 136.3, 135.6, 133.9, 133.4, 129.0, 125.5, 121.9, 56.2, 50.2, 39.1, 35.6, 27.5, 27.0, 23.6, 23.1, 13.8, 0.0, −0.2, −1.3, −1.6; $^{29}$Si NMR (120 MHz, CDCl$_3$) δ 16.93, 12.98; IR (cm$^{-1}$): 2955, 1560, 1463, 1334, 1252, 1210, 1191, 1161, 996, 829, 782; HRMS (FAB): Calculated for C$_{22}$H$_{35}$N$_2$O$_3$SSi$_2$ [M+H]$^+$: 463.1907. Found: 463.1904.

[Example 41] Preparation of 2,2,4,4-tetramethyl-1-phenyl-7-(quinolin-8-ylsulfonyl)-3-oxa-7-aza-2,4-disilabicyclo[3.3.1]nonane (40b)

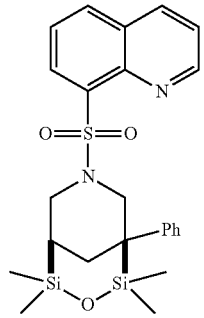

2,2,4,4-tetramethyl-1-phenyl-7-(quinolin-8-ylsulfonyl)-3-oxa-7-aza-2,4-disilabicyclo[3.3.1]nonane (40b) was obtained by the same method as Example 39 above except for using 3-phenyl pyridine (39a) instead of 3-methyl pyridine (35a).

White solid; m.p. 111-113° C.; $^1$H NMR (600 MHz, CDCl$_3$) δ 9.01 (dd, J=4.2, 1.8 Hz, 1H), 8.53 (dd, J=7.4, 1.4 Hz, 1H), 8.17 (dd, J=8.3, 1.8 Hz, 1H), 7.99 (dd, J=8.2, 1.4 Hz, 1H), 7.61 (t, J=7.8 Hz, 1H), 7.44 (dd, J=8.2, 4.2 Hz, 1H), 7.26 (dd, J=8.4, 7.2 Hz, 2H), 7.20-7.15 (m, 2H), 7.14-7.08 (m, 1H), 4.85 (dt, J=11.9, 1.8 Hz, 1H), 4.30-4.24 (m, 1H), 2.71 (dt, J=13.4, 2.2 Hz, 1H), 2.65 (dd, J=11.7, 3.5 Hz, 1H), 2.41 (d, J=11.9 Hz, 1H), 1.73 (dd, J=13.5, 5.0 Hz, 1H), 1.14-1.09 (m, 1H), 0.54 (s, 3H), 0.48 (s, 3H), 0.17 (s, 3H), −0.42 (s, 3H); $^{13}$C NMR (150 MHz, CDCl$_3$) δ 151.1, 144.7, 144.5, 136.2, 135.6, 134.0, 133.5, 128.9, 128.3 (2C), 125.4, 125.2, 125.2 (2C), 121.8, 55.6, 49.9, 33.5, 32.0, 23.2, 0.1, −1.2, −1.6, −2.9; $^{29}$Si NMR (80 MHz, CDCl$_3$) δ 13.46, 13.10; IR (cm$^{-1}$): 2816, 1492, 1332, 1243, 1158, 1141, 1001, 829, 789, 759; HRMS (FAB): Calculated for C$_{24}$H$_{31}$N$_2$O$_3$SSi$_2$ [M+H]$^+$: 483.1594. Found: 483.1597.

[Example 42] Preparation of 1-benzyl-1,2,3,4-tetrahydrobenzo[h]quinolin-3-ol (42)

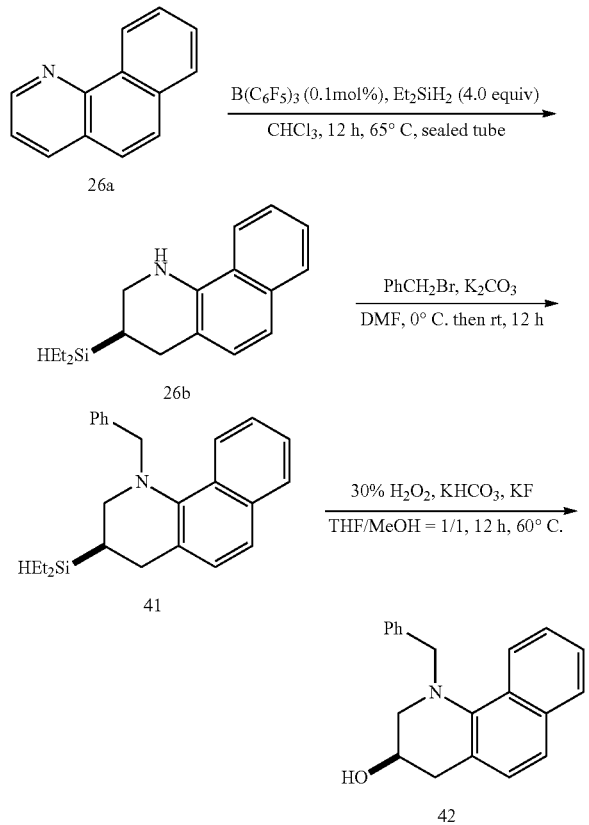

Preparation of Compound 26b

B(C$_6$F$_5$)$_3$ (0.0080 mmol, 0.10 mol %) was dissolved in chloroform (3.0 mL) in a 15 mL sealed tube, then diethylsilane (32 mmol, 4.0 eq) was added thereto. A solution of compound 26a (8.0 mmol, 1.0 eq) dissolved in chloroform (5.0 mL) was added to the above-prepared solution. The reaction mixture was stirred at 65° C. for 12 hours, cooled to room temperature, and filtrated by passing through a silica gel pad with dichloromethane (50 mL) and methanol (5 mL). After decompression concentration of the filtrate, the obtained residue was purified by silica gel column chromatography (EA/Hx=5/95) to obtain a compound 26b (colorless oil, 2.0 g, 95%).

Preparation of Compound 41

A compound 26b (7.4 mmol, 1.0 eq) was dissolved in N,N-dimethylformamide (21 mL), then K$_2$CO$_3$ (22 mmol, 3.0 eq) and benzyl bromide (8.9 mmol, 1.2 eq) were drop-wide added thereto at 0° C. for 10 mins. The reaction mixture was stirred at room temperature for 12 hours, and water (20 mL) was added thereto to thereby complete the reaction. Next, the reaction mixture was extracted with diethylether (20 mL×2), the obtained organic layer was washed with saturated ammonium chloride solution (40 mL), dried with anhydrous MgSO$_4$, followed by filtration and decompression concentration, and the residue was purified by silica gel column chromatography (EA/Hx=1/10) to obtain a compound 41 (2.5 g, 95%).

Brown oil; $^1$H NMR (600 MHz, CDCl$_3$) δ 8.34-8.29 (m, 1H), 7.90-7.85 (m, 1H), 7.76-7.71 (m, 2H), 7.58-7.51 (m, 3H), 7.51-7.43 (m, 3H), 7.27 (d, J=8.4 Hz, 1H), 4.68 (d, J=16.1 Hz, 1H), 4.18 (d, J=16.0 Hz, 1H), 3.77 (q, J=3.1 Hz, 1H), 3.38 (ddd, J=13.7, 2.7, 1.5 Hz, 1H), 3.14 (ddd, J=13.8, 12.5, 1.5 Hz, 1H), 3.07-2.99 (m, 2H), 1.80 (dt, J=5.6, 2.7 Hz, 1H), 1.13 (dt, J=19.4, 7.9 Hz, 6H), 0.79 (dd, J=7.9, 3.2 Hz, 4H); $^{13}$C NMR (150 MHz, CDCl$_3$) δ 144.1, 139.5, 133.4, 128.9, 128.6 (2C), 128.3, 127.8, 127.4 (2C), 127.0, 125.7, 125.2, 124.9, 122.8, 122.0, 58.9, 49.0, 30.1, 11.2, 8.4, 8.3, 1.2, 1.1; $^{29}$Si NMR (120 MHz, CDCl$_3$) δ 0.16; IR (cm$^{-1}$): 3047, 2950, 2871, 2090, 1601, 1569, 1451, 1395, 1359, 1028, 801; HRMS (EI): Calculated for C$_{24}$H$_{29}$NSi [M]$^+$: 359.2069. Found: 359.2067.

Preparation of Compound 42

A compound 41 (7.0 mmol, 1.0 eq), KF (42 mmol, 6.0 eq), KHCO$_3$ (42 mmol, 6.0 eq), 30% aqueous hydrogen peroxide solution (130 mmol, 18 eq), and tetrahydrofuran (59 mL) were mixed with methanol (59 mL), and stirred at 60° C. for 12 hours. 10% NaHSO$_3$ aqueous solution (20 mL) was added to the reaction mixture at 0° C., and extracted with diethylether (60 mL×3). The obtained organic layer was washed with saturated Na$_2$CO$_3$ aqueous solution (60 mL×2), dried with anhydrous MgSO$_4$, followed by filtration and decompression concentration, and the residue was purified by silica gel column chromatography (EA/Hx=1/1) to obtain a compound 42 (1.8 g, 91%).

Colorless solid; m.p. 62-64° C.; $^1$H NMR (600 MHz, CDCl$_3$) δ 8.14-8.04 (m, 1H), 7.81 (d, J=7.7 Hz, 1H), 7.60 (d, J=7.6 Hz, 2H), 7.53-7.44 (m, 3H), 7.38 (d, J=8.0 Hz, 3H), 7.18 (d, J=8.4 Hz, 1H), 4.69 (d, J=16.3 Hz, 1H), 4.36-4.27 (m, 1H), 4.24 (d, J=16.3 Hz, 1H), 3.42-3.22 (m, 2H), 2.99 (dd, J=13.1, 9.8 Hz, 1H), 2.92-2.76 (m, 1H), 1.93-1.58 (m, 1H); $^{13}$C NMR (150 MHz, CDCl$_3$) δ 142.7, 139.2, 133.7, 128.7 (2C), 128.4, 128.0, 127.8, 127.2 (2C), 127.1, 125.4, 125.2, 123.1, 122.6, 122.5, 61.1, 60.0, 53.3, 37.6; IR (cm$^{-1}$): 3337, 3050, 2922, 2836, 1569, 1463, 1452, 1397, 1052, 804, 733; HRMS (EI): Calculated for C$_{20}$H$_{19}$NO [M]$^+$: 289.1467. Found: 289.1464.

[Example 43] Preparation of (3S,4S)-4-((S)-1-Hydroxyethyl)-1,2,3,4-tetrahydroquinolin-3-ol (47)

Preparation of 1-(quinolin-4-yl)ethan-1-ol

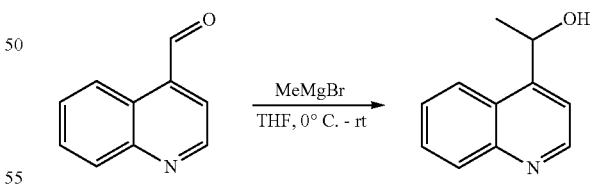

4-quinolinecarboxaldehyde (12 mmol, 1.0 eq) was added to tetrahydrofuran (60 mL) and stirred at 0° C., then 3.0 M methylmagnesium bromide solution in diethylether (13 mmol, 1.1 eq) was dropwise added thereto at room temperature. The reaction mixture was stirred at room temperature for 12 hours, and saturated ammonium chloride solution (20 mL) was added thereto to thereby complete the reaction. Then, water (40 mL) and ethyl acetate (30 mL) were added thereto, and extracted with ethyl acetate (60 mL×2). The obtained organic layer was dried with anhydrous MgSO$_4$, followed by filtration and decompression concentration, and the residue was purified by silica gel column chromatography (EA/Hx=1/1) to obtain 1-(quinolin-4-yl)ethan-1-ol (1.8 g, 87%).

White solid; m.p. 119-121° C.; $^1$H NMR (600 MHz, CDCl$_3$) δ 8.70 (s, 1H), 8.05 (d, J=8.5 Hz, 1H), 7.98 (d, J=8.5 Hz, 1H), 7.64 (t, J=7.9 Hz, 1H), 7.55 (s, 1H), 7.50 (t, J=7.8 Hz, 1H), 5.63 (d, J=7.8 Hz, 1H), 1.62 (d, J=6.5 Hz, 3H); $^{13}$C NMR (150 MHz, CDCl$_3$) δ 151.9, 150.2, 147.8, 129.9, 129.0, 126.5, 125.3, 123.0, 116.7, 65.8, 24.6; IR (cm$^{-1}$) 3349, 2976, 2928, 1666, 1592, 1510, 1239, 1168, 1121, 1073, 1017, 856, 763; HRMS (EI): Calculated for C$_{11}$H$_{11}$NO [M]$^+$: 173.0841. Found: 173.0841.

Preparation of (S)-1-(quinolin-4-yl)ethan-1-ol

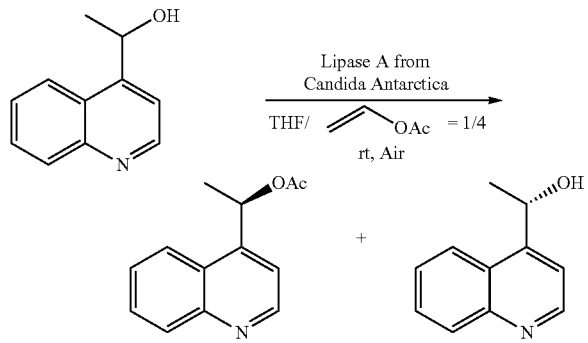

Tetrahydrofuran (10 mL), vinyl acetate (40 mL) and racemic alcohol starting material (10 mmol, 1.0 eq) were mixed, and lipase A from *Candida Antarctica*, CLEA (≥1 U/mg, Sigma, 560 mg) was added thereto at room temperature. The reaction mixture was stirred under open flask condition for 8 hours, and filtrated. After decompression concentration of the obtained filtrate, the residue was purified by silica gel column chromatography (EA/Hx=1/1) to obtain (S)-1-(quinolin-4-yl)ethan-1-ol (560 mg, 31%, ee=98% based on HPLC).

$^1$H NMR (600 MHz, CDCl$_3$) δ 8.58 (d, J=4.6 Hz, 1H), 7.96 (dd, J=8.4, 1.3 Hz, 1H), 7.91 (dd, J=8.6, 1.4 Hz, 1H), 7.60-7.50 (m, 2H), 7.46-7.38 (m, 1H), 5.58 (q, J=6.5 Hz, 1H), 1.58 (d, J=6.6 Hz, 3H); ee determination condition: Chiralcel IF, Hexane:EtOH=90:10, Flow=1.0 ml/min; $[α]_D^{25}$—87.2 (c=1.19, CHCl$_3$).

Preparation of (S)-4-[1-{(triisopropylsilyl)oxy}ethyl]quinoline ((S)-45a)

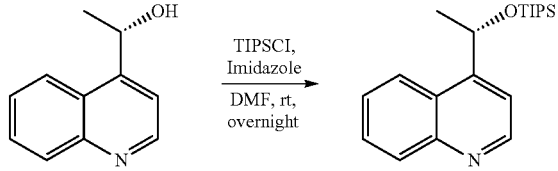

(S)-1-(quinolin-4-yl)ethan-1-ol (2.3 mmol, 1.0 eq) was added to N,N-dimethylformamide (6.0 mL), then imidazole (5.8 mmol, 2.5 eq) and triisopropylsilyl chloride (3.5 mmol, 1.5 eq) were added thereto at room temperature. The reaction mixture was stirred overnight, and water (6 mL) was added thereto to thereby complete the reaction, then extracted with diethylether (10 mL×3), and dried with anhydrous MgSO$_4$, followed by filtration and decompression concentration, and the residue was purified by silica gel column chromatography (EA/Hx=1/10) to obtain (S)-4-[1-{(triisopropylsilyl)oxy}ethyl]quinoline ((S)-45a) which is a silylether compound (586 mg, 77%).

Colorless oil; $^1$H NMR (600 MHz, CDCl$_3$) δ 8.91 (d, J=4.3 Hz, 1H), 8.13 (d, J=8.4 Hz, 1H), 8.00 (d, J=8.4 Hz, 1H), 7.76-7.60 (m, 2H), 7.53 (t, J=7.7 Hz, 1H), 5.68 (d, J=6.3 Hz, 1H), 1.58 (d, J=6.1 Hz, 3H), 1.14 (d, J=7.7 Hz, 3H), 1.06 (dd, J=7.3, 3.2 Hz, 9H), 1.05-0.95 (m, 9H); $^{13}$C NMR (150 MHz, CDCl$_3$) δ 152.5, 150.5, 148.2, 130.3, 128.8, 126.2, 125.0, 122.9, 117.3, 67.3, 26.7, 18.0 (6C), 12.2 (3C); IR (cm$^{-1}$) 2942, 2865, 1592, 1509, 1462, 1369, 1297, 1239, 1208, 1168, 1121, 1091, 1038, 947, 881, 845, 758, 724, 678, 559, 451; HRMS (FAB): Calculated for C$_{20}$H$_{32}$NOSi [M+H]$^+$: 330.2253. Found: 330.2251.

Preparation of (3R,4S)-3-(diethylsilyl)-4-[(S)-1-{(triisopropylsilyl)oxy}ethyl]-1,2,3,4-tetrahydroquinoline (45b)

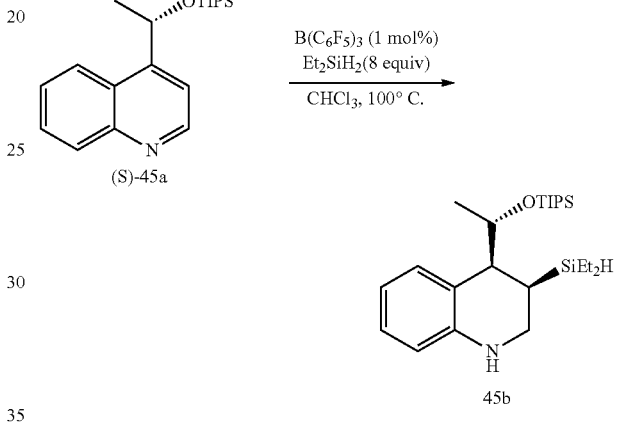

B(C$_6$F$_5$)$_3$ (0.0050 mmol, 1.0 mol %) was dissolved in chloroform (0.25 mL) in a 2.5 mL reaction vial, then diethylsilane (4.4 mmol, 8.0 eq) was added thereto. A quinoline compound (S)-45a (0.55 mmol, 1.0 eq) dissolved in chloroform (0.3 mL) was added to the above-prepared solution, and stirred at 100° C. for 12 hours, cooled to room temperature, and filtrated by passing through a silica gel pad with dichloromethane (15 mL) and methanol (2 mL). After decompression concentration of the filtrate, the residue was purified by silica gel column chromatography (EA/Hx=1/20) to obtain (3R,4S)-3-(diethylsilyl)-4-[(S)-1-{(triisopropylsilyl)oxy}ethyl]-1,2,3,4-tetrahydroquinoline (45b) (159 mg, 69%).

Colorless oil; $^1$H NMR (600 MHz, CDCl$_3$) δ 7.09 (dd, J=7.6, 1.5 Hz, 1H), 7.03-6.90 (m, 1H), 6.58 (td, J=7.4, 1.2 Hz, 1H), 6.43 (dd, J=8.0, 1.2 Hz, 1H), 4.14 (t, J=6.2 Hz, 1H), 3.86 (s, br, 1H), 3.66 (dd, J=11.3, 4.5 Hz, 1H), 3.48 (q, J=3.1 Hz, 1H), 3.22 (dd, J=11.4, 3.0 Hz, 1H), 2.67 (dd, J=6.4, 2.3 Hz, 1H), 1.85 (dd, J=4.6, 2.6 Hz, 1H), 1.22 (d, J=6.1 Hz, 3H), 1.04 (d, J=5.8 Hz, 21H), 0.99-0.89 (m, 6H), 0.66-0.46 (m, 4H); $^{13}$C NMR (150 MHz, CDCl$_3$) δ 145.3, 131.3, 127.1, 121.2, 116.3, 113.9, 72.4, 46.0, 40.3, 22.0, 18.24 (3C), 18.22 (3C), 17.3, 12.9 (3C), 8.42, 8.38, 1.8, 1.7; $^{29}$Si NMR (120 MHz, CDCl$_3$) δ 10.07, 1.44; IR (cm$^{-1}$) 2943, 2866, 2089, 1607, 1501, 1462, 1371, 1351, 1315, 1274, 1258, 1236, 1121, 1058, 1002, 920, 882, 806, 744, 673, 495; HRMS (EI): Calculated for C$_{24}$H$_{45}$NOSi$_2$ [M]$^+$: 419.3040. Found: 419.3036; $[α]_D^{25}$—18.9 (c=1.0, CHCl$_3$).

Preparation of (3S,4S)-4-((S)-1-Hydroxyethyl)-1,2,3,4-tetrahydroquinolin-3-ol (47)

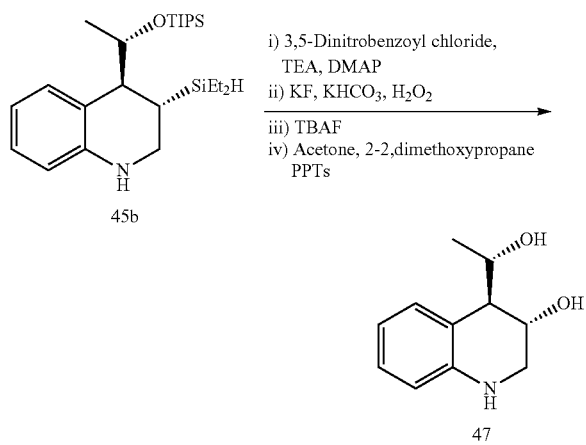

A compound 45b (0.35 mmol, 1.0 eq), triethylamine (0.88 mmol, 2.5 eq), 3,5-dinitrobenzoyl chloride (0.53 mmol, 1.5 eq) and 4-(dimethylamino)-pyridine (0.18 mmol, 0.50 eq) were sequentially added to dichloromethane (3.0 mL) at room temperature, and stirred at room temperature for 2 hours. Saturated aqueous $NaHCO_3$ solution (4 mL) was added thereto to thereby complete the reaction, and extracted with ethyl acetate (4 mL×3). The obtained organic layer was dried with anhydrous $MgSO_4$, followed by filtration and decompression concentration, and the residue was purified by silica gel column chromatography (EA/Hx=1/10) to obtain corresponding amide product (step i).

Tetrahydrofuran (1.5 mL) and methanol (1.5 mL) were added to the obtained amide product (0.29 mmol, 1.0 eq), then KF (0.87 mmol, 3.0 eq), $KHCO_3$ (0.87 mmol, 3.0 eq) and 30% aqueous hydrogen peroxide solution (2.6 mmol, 9.0 eq) were added thereto at room temperature. The reaction mixture was stirred at 60° C. for 8 hours, then saturated $Na_2SO_3$ aqueous solution (5 mL) was added thereto to thereby complete the reaction. Next, the reaction mixture was extracted with ethyl acetate (5 mL×3), the obtained organic layer was dried with anhydrous $MgSO_4$, followed by filtration and decompression concentration, and the residue was purified by silica gel column chromatography (EA/Hx=1/1) to obtain a corresponding secondary alcohol product 46 as a white solid (ee=98% based on HPLC) (step ii).

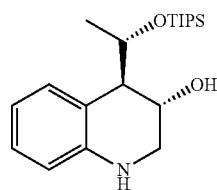

46 ee determination condition: Chiralcel ID, Hexane:IPA=80:20, Flow=1.0 ml/min.

The obtained secondary alcohol product 46 (0.092 mmol, 1.0 eq) was added to tetrahydrofuran (1.0 mL), then 1.0 M tetrabutylammonium fluoride solution in tetrahydrofuran (0.14 mmol, 1.5 eq) was added thereto at room temperature. The reaction mixture was stirred at room temperature for 16 hours, followed by decompression concentration. The residue was purified by silica gel column chromatography (EA) to obtain a corresponding diol product 47 (step iii) (6.2 mg, 35% in 3 steps).

White solid; m.p. 143-145° C.; $^1$H NMR (600 MHz, $CD_3OD$) δ 7.00 (dd, J=7.6, 1.5 Hz, 1H), 6.98-6.90 (m, 1H), 6.57-6.46 (m, 2H), 4.35 (d, J=3.2 Hz, 1H), 3.69 (dd, J=8.2, 6.3 Hz, 1H), 3.44 (dd, J=12.6, 2.7 Hz, 1H), 3.26-3.18 (m, 1H), 2.65 (ddd, J=8.3, 3.4, 1.6 Hz, 1H), 1.18 (d, J=6.3 Hz, 3H); $^{13}$C NMR (100 MHz, $CD_3OD$) δ 145.9, 133.0, 128.5, 120.0, 117.2, 115.0, 71.3, 64.5, 53.51, 45.5, 22.1; IR (cm$^{-1}$) 3302, 1603, 1580, 1500, 1370, 1319, 1284, 1253, 1225, 1127, 1105, 1056, 1020, 929, 875, 784, 744, 723, 655, 510; HRMS (ESI): Calculated for $C_{11}H_{16}NO_2$ [M+H]$^+$: 194.1176. Found: 194.1153.

The invention claimed is:

1. A method of preparing a silylative-reduced N-heterocyclic compound by reducing an N-heteroaromatic compound including a central ring having 5 to 20 carbon atoms and a sp$^2$ hybridized nitrogen atom while simultaneously introducing a silyl group into a beta-position with respect to a nitrogen atom of the N-heteroaromatic compound, using a silane compound, in the presence of an organoboron catalyst.

2. The method of claim 1, wherein an N-heterocyclic compound represented by the following Chemical Formula 1-1 is prepared by reacting a quinoline compound represented by the following Chemical Formula 2-1 with a silane compound represented by the following Chemical Formula 3-1, in the presence of the organoboron catalyst:

[Chemical Formula 1-1]

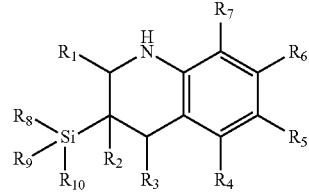

[Chemical Formula 2-1]

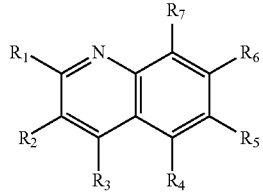

[Chemical Formula 3-1]

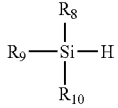

in Chemical Formulas 1-1, 2-1, and 3-1, $R_1$ to $R_7$ are each independently hydrogen, (C1-C10) alkyl, (C1-C10)alkoxy, (C6-C12)aryl, halogen or (C6-C12)aryloxy, or the $R_4$ to $R_7$ may be each independently linked to an adjacent substituent via (C3-C12) alkenylene with or without a fused ring to form a monocyclic or polycyclic aromatic ring, and the alkyl, aryl and aryloxy of $R_1$ to $R_7$ may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

3. The method of claim 1, wherein an N-heterocyclic compound represented by the following Chemical Formula 1-2 is prepared by reacting an isoquinoline compound represented by the following Chemical Formula 2-2 with a silane compound represented by the following Chemical Formula 3-1, in the presence of the organoboron catalyst:

[Chemical Formula 1-2]

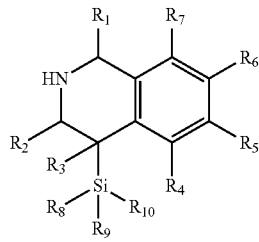

[Chemical Formula 2-2]

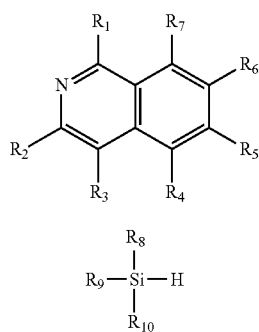

[Chemical Formula 3-1]

$$R_9-\underset{\underset{R_{10}}{|}}{\overset{\overset{R_8}{|}}{Si}}-H$$

in Chemical Formulas 1-2, 2-2, and 3-1, $R_1$ to $R_7$ are each independently hydrogen, (C1-C10)alkyl, (C1-C10)alkoxy, (C6-C12)aryl, halogen or (C6-C12)aryloxy, or the $R_4$ to $R_7$ may be each independently linked to an adjacent substituent via (C3-C12) alkenylene with or without a fused ring to form a monocyclic or polycyclic aromatic ring, and the alkyl, aryl and aryloxy of $R_1$ to $R_7$ may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

4. The method of claim 1, wherein an N-heterocyclic compound represented by the following Chemical Formula 1-3 is prepared by reacting a pyridine compound represented by the following Chemical Formula 2-3 with a silane compound represented by the following Chemical Formula 3-1, in the presence of the organoboron catalyst:

[Chemical Formula 1-3]

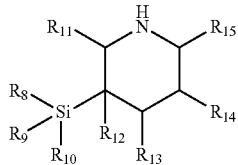

[Chemical Formula 2-3]

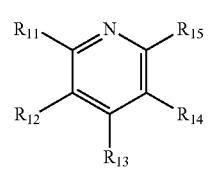

[Chemical Formula 3-1]

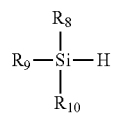

in Chemical Formulas 1-3, 2-3, and 3-1, $R_{11}$ to $R_{15}$ are each independently hydrogen, (C1-C10)alkyl, (C1-C10)alkoxy, (C6-C12)aryl, halogen or (C6-C12)aryloxy, and the alkyl, aryl and aryloxy of $R_{11}$ to $R_{15}$ may be further substituted with (C1-C10)alkyl;

$R_8$ and $R_9$ are each independently (C1-C10)alkyl or (C6-C12)aryl; and $R_{10}$ is hydrogen or (C6-C12)aryl;

provided that $R_8$, $R_9$ and $R_{10}$ are not (C6-C12)aryl at the same time.

5. The method of claim 1, wherein the organoboron catalyst is $B(C_6F_5)_3$ or $B(C_6F_5)_2Ar$, and the Ar is (C6-C12)aryl.

6. The method of claim 1, wherein the organoboron catalyst is used at 0.1 to 5.0 mol % based on 1 mol of the N-heteroaromatic compound.

7. The method of claim 6, wherein the organoboron catalyst is used at 1.0 to 5.0 mol % based on 1 mol of the N-heteroaromatic compound.

8. The method of claim 1, wherein the silane compound is used in amounts of 4 to 8 mol based on 1 mol of the N-heteroaromatic compound.

9. The method of claim 1, wherein the silylative-reduction is performed at a reaction temperature of 23 to 100° C.

10. The method of claim 1, wherein the silylative-reduction is performed by using one or two or more solvents selected from the group consisting of chloroform, dichloromethane, toluene, chlorobenzene, benzene, hexane and dichloroethane.

* * * * *